United States Patent
Sonobe et al.

(10) Patent No.: US 12,427,122 B2
(45) Date of Patent: Sep. 30, 2025

(54) METHOD OF MAKING TRANSDERMAL AMPHETAMINE COMPOSITION WITH LOW LEVELS OF CARBAMATE

(71) Applicant: Noven Pharmaceuticals, Inc., Miami, FL (US)

(72) Inventors: Atsushi Sonobe, Miami, FL (US); Deboprosad Mondal, Miami, FL (US); Naruhito Higo, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 463 days.

(21) Appl. No.: 18/092,761

(22) Filed: Jan. 3, 2023

(65) Prior Publication Data

US 2023/0201139 A1  Jun. 29, 2023

Related U.S. Application Data

(62) Division of application No. 17/569,862, filed on Jan. 6, 2022, now Pat. No. 11,559,501.

(60) Provisional application No. 63/134,847, filed on Jan. 7, 2021.

(51) Int. Cl.
| | | |
|---|---|---|
| *A61K 31/137* | (2006.01) | |
| *A61K 9/51* | (2006.01) | |
| *A61K 9/70* | (2006.01) | |

(52) U.S. Cl.
CPC ............ *A61K 31/137* (2013.01); *A61K 9/51* (2013.01); *A61K 9/7023* (2013.01)

(58) Field of Classification Search
None
See application file for complete search history.

(56) References Cited

U.S. PATENT DOCUMENTS

| | | |
|---|---|---|
| 3,742,022 A | 6/1973 | Verbiscar |
| 7,993,671 B2 | 8/2011 | Mantelle et al. |
| 8,187,628 B2 | 5/2012 | Houze et al. |
| 8,343,538 B2 | 1/2013 | Kanios et al. |
| 8,591,941 B2 | 11/2013 | Kanios et al. |
| 8,703,175 B2 | 4/2014 | Kanios et al. |
| 8,815,281 B2 | 8/2014 | Kanios et al. |
| 9,155,712 B2 | 10/2015 | Kanios et al. |
| 9,333,263 B2 | 5/2016 | Kanios |
| 9,456,993 B2 | 10/2016 | Lambert |
| 9,474,722 B2 | 10/2016 | Lambert |
| 9,901,552 B2 | 2/2018 | Lambert |

(Continued)

FOREIGN PATENT DOCUMENTS

| | | |
|---|---|---|
| CN | 101398414 A | 4/2009 |
| CN | 107478755 A | 12/2017 |

(Continued)

OTHER PUBLICATIONS

Buckley et al., "a-Amino Acids as Chiral Educts for Asymmetric Products. Amino Acylation with N-Acylamino Acids," Journal of the American Chemical Society, vol. 103, No. 20, pp. 6157-6163 (1981) XP055906492.

(Continued)

*Primary Examiner* — Isis A Ghali
(74) *Attorney, Agent, or Firm* — Foley & Lardner LLP

(57) ABSTRACT

Described are methods for reducing the formation of amphetamine carbamate and amphetacarbamate in transdermal amphetamine compositions, compositions with low levels of amphetacarbamate, and methods using such compositions for transdermal delivery of amphetamine.

27 Claims, 15 Drawing Sheets

(56) References Cited

U.S. PATENT DOCUMENTS

| | | |
|---|---|---|
| 10,004,696 B2 | 6/2018 | Lambert |
| 10,231,938 B2 | 3/2019 | Kanios et al. |
| 10,406,115 B2 | 9/2019 | Zhang et al. |
| 10,406,116 B2 | 9/2019 | Zhang et al. |
| 11,559,501 B2 | 1/2023 | Sonobe et al. |
| 11,572,339 B2 | 2/2023 | Mondal |
| 11,976,026 B2 | 5/2024 | Mondal |
| 2005/0019385 A1 | 1/2005 | Houze |
| 2005/0169977 A1 | 8/2005 | Kanios et al. |
| 2014/0271865 A1 | 9/2014 | Lambert et al. |
| 2014/0288038 A1 | 9/2014 | Kanios |
| 2014/0322298 A1 | 10/2014 | Nguyen et al. |
| 2015/0104495 A1 | 4/2015 | Nguyen et al. |
| 2015/0342899 A1 | 12/2015 | Kulakofsky et al. |
| 2016/0030362 A1 | 2/2016 | Liao et al. |
| 2016/0256406 A1 | 9/2016 | Liu et al. |
| 2017/0065535 A1 | 3/2017 | Kanios |
| 2018/0207280 A1 | 7/2018 | Nguyen et al. |
| 2018/0243242 A1 | 8/2018 | Lambert |
| 2020/0277424 A1 | 9/2020 | Liao et al. |
| 2023/0201139 A1 | 6/2023 | Sonobe et al. |

FOREIGN PATENT DOCUMENTS

| | | |
|---|---|---|
| CN | 109507339 A | 3/2019 |
| WO | WO-2005/042055 A2 | 5/2005 |
| WO | WO-2014/066585 A1 | 5/2014 |
| WO | WO-2014/105783 A1 | 7/2014 |

OTHER PUBLICATIONS

International Search Report and Written Opinion in PCT Appl. No. PCT/US2022/011377 dated May 13, 2022 (14 pages).
Jonsson et al., "A Convenient Derivatization Method for the Determination of Amphetamine and Related Drugs in Urine", Journal of Forensic Science, vol. 41, No. 1, pp. 148-151, (Jan. 1996) XP008091783.
Neish; "Substituted ammonium carbamates from alpha,beta-diarylethyl amines", Recueil Des Travaux Chimiques Des Pays-Bas, vol. 68, No. 5, 1949, pp. 491-494, XP055931889.
Partial International Search Report in Application No. PCT/US2022/011378 dated Apr. 11, 2022.
Shriner, et al; "The synthesis of N-substituted carbamates", Journal of the Amercian Chemical Society, 74(2):549-550 (Jan. 20, 1952).
Thurbide et al.; "Discrimination of structural isomers of amphetamine using carbon dioxide negative-ion chemical ionization mass spectrometry", Spectroscopy, 13(2): 151-161 (1997).
Wright, et al.; "Reactions of aralkyl amines with carbon dioxide", Journal of the American Chemical Society, Nov. 1, 1948 (Nov. 1, 1948), pp. 3865-3866, XP055931915.

METHOD OF MAKING TRANSDERMAL AMPHETAMINE COMPOSITION WITH LOW LEVELS OF CARBAMATE

CROSS-REFERENCE TO RELATED APPLICATIONS

The present application is a divisional application of U.S. application Ser. No. 17/569,862 filed on Jan. 6, 2022, which claims priority to U.S. provisional application 63/134,847, filed Jan. 7, 2021, the entire contents of which are incorporated herein by reference.

The present application claims priority to U.S. provisional application 63/134,847, filed Jan. 7, 2021, the entire contents of which are incorporated herein by reference.

FIELD

The present disclosure relates generally to the transdermal delivery of amphetamine, such as may be desired for achieving central nervous system stimulation, such as for the treatment of attention deficit disorder (ADD), attention deficit hyperactivity disorder (ADHD), narcolepsy, or binge eating disorder. The present disclosure provides methods for reducing the formation of amphetamine carbamate (amphet-ammonium-amphetacarbamate) and amphetacarbamate in transdermal amphetamine compositions, transdermal amphetamine compositions and amphetamine transdermal delivery systems with low levels of amphetamine carbamate and amphetacarbamate, and methods using them for the transdermal delivery of amphetamine.

BACKGROUND

Attention-deficit/hyperactivity disorder (ADHD) is a neurobehavioral disorder that typically begins in childhood and often persists into adulthood. ADHD is characterized by developmentally inappropriate levels of inattention, impulsivity, and hyperactivity. Although individuals with this disorder can be very successful in life, without identification and proper treatment, ADHD may have serious consequences, including school failure, family stress and disruption, depression, problems with relationships, substance abuse, delinquency, risk for accidental injuries and job failure. Thus, early identification and treatment can be extremely important to a subject's quality of life.

ADHD is the most common developmental disorder of childhood, affecting about 3 to 5% of children globally and diagnosed in about 2 to 16% of school aged children. In addition, it is estimated that 4.7% of American adults live with ADHD. Amphetamine products currently approved for use in the U.S. for the treatment of ADHD are oral dosage forms, including ADDERALL XR® (amphetamine, d-amphetamine mixed salts) and VYVANSE® (lisdexamfetamine) (a prodrug of amphetamine).

Transdermal amphetamine compositions and amphetamine transdermal delivery systems have been described in previous patents and patent applications, for example, in U.S. Pat. Nos. 7,993,671; 8,632,802; 8,216,606; 9,034,370; 8,337,884; 8,187,628; 8,916,191; 8,591,941; 8,815,281; 9,155,712; 10,231,938; 9,333,263; 9,456,993; 9,474,722; 9,901,552; 10,004,696, U.S. Patent Application Publication 2015/0104495; U.S. Pat. Nos. 8,703,175; 9,295,726; U.S. Patent Application Publication 2015/0342899. However, there is no approved transdermal amphetamine product. Thus, there remains a need for transdermal amphetamine compositions and amphetamine transdermal delivery systems. For potency and safety reasons, there is a particular need for transdermal amphetamine compositions and amphetamine transdermal delivery systems that have at most low levels of amphetamine-related compounds, including the newly discovered amphetamine-related compounds, amphetamine carbamate and amphetacarbamate.

SUMMARY OF THE INVENTION

Provided herein are transdermal amphetamine compositions with a low amphetamine carbamate content, comprising a drug-containing polymer matrix comprising a therapeutically effective amount of amphetamine in a pressure-sensitive adhesive polymer matrix, wherein the drug-containing polymer matrix has an amphetacarbamate content of no more than 5.0% w/w of the target amphetamine content. In some embodiments, the drug-containing polymer matrix has an amphetacarbamate content of no more than 1.0% w/w, based on the total dry weight of the drug-containing polymer matrix (% w/w dry). In some embodiments, the drug-containing polymer matrix has an amphetacarbamate content of no more than 5% w/w of the actual amphetamine content of the drug-containing polymer matrix.

Also provided are transdermal amphetamine compositions with a low amphetamine carbamate content, comprising a drug-containing polymer matrix comprising a therapeutically effective amount of amphetamine in a pressure-sensitive adhesive polymer matrix, wherein the drug-containing polymer matrix has an amphetacarbamate content of no more than 1.0% w/w, based on the total dry weight of the drug-containing polymer matrix (% w/w dry), no more than 10% w/w of the actual amphetamine content of the drug-containing polymer matrix, and/or no more than 10% w/w of the target amphetamine content of the drug-containing polymer matrix at the time of manufacture.

Also provided herein are methods of making a transdermal amphetamine composition with reduced amphetacarbamate content, comprising preparing a transdermal amphetamine composition comprising a drug-containing polymer matrix comprising a therapeutically effective amount of amphetamine in a pressure-sensitive adhesive polymer matrix under conditions that limit exposure to $CO_2$, wherein the drug-containing polymer matrix has an amphetacarbamate content selected from one or more of no more than 1.0% w/w, based on the total dry weight of the drug-containing polymer matrix (% w/w dry), no more than 5% w/w of the actual amphetamine content of the drug-containing polymer matrix, and no more than 5% w/w of the target amphetamine content of the drug-containing polymer matrix at the time of manufacture.

Also provided are methods of making a transdermal amphetamine composition with reduced amphetamine carbamate content, comprising preparing a transdermal amphetamine composition comprising a drug-containing polymer matrix comprising a therapeutically effective amount of amphetamine in a pressure-sensitive adhesive polymer matrix under conditions that limit exposure to $CO_2$, wherein the drug-containing polymer matrix has an amphetacarbamate content of no more than 1.0% w/w, based on the total dry weight of the drug-containing polymer matrix (% w/w dry), no more than 10% w/w of the actual amphetamine content of the drug-containing polymer matrix, and/or no more than 10% w/w of the target amphetamine content of the drug-containing polymer matrix at the time of manufacture.

The methods may comprise a process comprising (i) preparing a drug-containing polymer matrix blend by blending the polymer matrix components and drug (amphetamine) in a suitable solvent; (ii) coating the blend onto a release liner; and (iii) drying the blend in an oven to remove the solvent(s), thereby obtaining dry drug-in-polymer matrix on a release liner; wherein the conditions that limit exposure to $CO_2$ are one or more selected from controlling the temperature of the manufacturing room; preparing the drug-containing polymer matrix under an inert gas; preparing the drug-containing polymer matrix blend in stages comprising a first stage comprising blending some or all of the polymer matrix components other than amphetamine and a subsequent stage comprising adding and blending in the amphetamine; adjusting the drying the temperature in the oven; adjusting air flow in the oven; and adjusting the speed at which the wet polymer matrix material travels along the processing line.

In some embodiments, the drug-containing polymer matrix has an amphetacarbamate content selected from no more than 1.0% w/w dry, no more than 0.9% w/w dry, no more than 0.8% w/w dry, no more than 0.75% w/w dry, no more than 0.7% w/w dry, no more than 0.6% w/w dry, no more than 0.5% w/w dry, no more than 0.4% w/w dry, no more than 0.3% w/w dry, no more than 0.2% w/w dry, no more than 0.1% w/w dry, no more than 0.05% w/w dry, and no more than 0.01% w/w dry. In some embodiments, the drug-containing polymer matrix has an amphetacarbamate content selected from 0.01%-1.0% w/w dry, 0.01%-0.9% w/w dry, 0.01%-0.8% w/w dry, 0.01%-0.75.% w/w dry, 0.01%-0.7% w/w dry, 0.01-0.6% w/w dry, 0.01%-0.5% w/w dry, 0.01-0.4% w/w dry, 0.01%-0.3% w/w dry, 0.01-0.2% w/w dry, 0.01-1.0% w/w dry, from 0.1%-0.8.% w/w dry, 0.1%-0.7% w/w dry, 0.1-0.6% w/w dry, 0.1%-0.5% w/w dry, 0.1-0.4% w/w dry, 0.1%-0.3% w/w dry, 0.1-0.2% w/w dry, or 0.1-1.0% w/w dry. In some embodiments, the drug-containing polymer matrix has an amphetacarbamate content selected from no more than 0.6% w/w dry, from 0.01-0.6% w/w dry, or from 0.1-0.6% w/w dry. In some embodiments, the drug-containing polymer matrix has an amphetacarbamate content selected from no more than 0.75% w/w dry, from 0.01-0.75% w/w dry, or from 0.1-0.75% w/w dry. In some embodiments, the drug-containing polymer matrix has an amphetacarbamate content selected from no more than 0.9% w/w dry, from 0.01-0.9% w/w dry, or from 0.1-0.9% w/w dry.

In some embodiments, at the time of manufacture the drug-containing polymer matrix has an amphetacarbamate content selected from no more than 5.0% w/w of the target amphetamine content, no more than 4.0% w/w of the target amphetamine content, no more than 3.0% w/w of the target amphetamine content, no more than 2.0% w/w of the target amphetamine content, or no more than 1.0% w/w of the target amphetamine content. In some embodiments, at the time of manufacture the drug-containing polymer matrix has an amphetacarbamate content of from 0.1-5.0% w/w, from 0.1-4.0% w/w, from 0.1%-3.0% w/w, from 0.1-2.0% w/w, or from 0.1-1.0% w/w, or less, of the target amphetamine content, or from 0.2-5.0% w/w, 0.2-4.0% w/w, from 0.2%-3.0% w/w, from 0.2-2.0% w/w, or from 0.2-1.0% w/w, or less, of the target amphetamine content, from 0.3-5.0% w/w, from 0.3-4.0% w/w, from 0.3-3.0% w/w, from 0.3-2.0% w/w, from 0.3-1.0% w/w, or less, of the target amphetamine content, from 0.4-5.0% w/w, from 0.4-4.0% w/w, from 0.4-3.0% w/w, from 0.4-2.0% w/w, from 0.4-1.0% w/w, or less, of the target amphetamine content, or from 0.5-5.0% w/w, from 0.5-4.0% w/w, from 0.5%-3.0% w/w, from 0.5%-2.0% w/w, or from 0.5%-1.0% w/w, or less, of the target amphetamine content, including about 3.0% w/w or less, or 3.0% w/w or less of the target amphetamine content.

In some embodiments, at the time of manufacture the drug-containing polymer matrix has an amphetacarbamate content selected from no more than 2.0-5.0% w/w of the target amphetamine content, no more than 2.0-4.0% w/w of the target amphetamine content, no more than 3.0-4.0% w/w of the target amphetamine content, no more than 5.0% w/w of the target amphetamine content, no more than 4.0% w/w of the target amphetamine content, no more than 3.0% w/w of the target amphetamine content, no more than 2.0% w/w of the target amphetamine content, from 0.1%-5.0% w/w, from 0.2%-5.0% w/w, from 0.3%-5.0% w/w, from 0.4%-5.0% w/w, or from 0.5%-5.0% w/w, or from 0.1%-4.0% w/w, from 0.2%-4.0% w/w, from 0.3%-4.0% w/w, from 0.4%-4.0% w/w, or from 0.5%-4.0% w/w, from 0.1%-3.0% w/w, from 0.2%-3.0% w/w, from 0.3%-3.0% w/w, from 0.4%-3.0% w/w, or from 0.5%-3.0% w/w, or from 0.1%-2.0% w/w, from 0.2%-2.0% w/w, from 0.3%-2.0% w/w, from 0.4%-2.0% w/w, or from 0.5%-2.0% w/w of the target amphetamine content. In some embodiments, at the time of manufacture the drug-containing polymer matrix has an amphetacarbamate content of no more than about 3.0% w/w of the target amphetamine content, such as no more than 3.0% w/w of the target amphetamine content.

In some embodiments, at the time of manufacture the drug-containing polymer matrix has an amphetacarbamate content selected from no more than 5.0% w/w of the actual amphetamine content, no more than 4.0% w/w of the actual amphetamine content, no more than 3.0% w/w of the actual amphetamine content, no more than 2.0% w/w of the actual amphetamine content, or no more than 1.0% w/w of the actual amphetamine content. In some embodiments, at the time of manufacture the drug-containing polymer matrix has an amphetacarbamate content of from 0.1-5.0% w/w, from 0.1-4.0% w/w, from 0.1%-3.0% w/w, from 0.1-2.0% w/w, or from 0.1-1.0% w/w, or less, of the actual amphetamine content, or from 0.2-5.0% w/w, from 0.2-4.0% w/w, from 0.2%-3.0% w/w, from 0.2-2.0% w/w, or from 0.2-1.0% w/w, or less, of the actual amphetamine content, or from 0.3-5.0% w/w, from 0.3-4.0% w/w, from 0.3-3.0% w/w, from 0.3-2.0% w/w, from 0.3-1.0% w/w, or less, of the actual amphetamine content, of from 0.4-5.0% w/w, from 0.4-4.0% w/w, from 0.4%-3.0% w/w, from 0.4%-2.0% w/w, or from 0.4%-1.0% w/w, or less, of the actual amphetamine content, or from 0.5-5.0% w/w, from 0.5-4.0% w/w, from 0.5%-3.0% w/w, from 0.5%-2.0% w/w, or from 0.5%-1.0% w/w, or less, of the actual amphetamine content. In some embodiments, at the time of manufacture the drug-containing polymer matrix has an amphetacarbamate content of no more than 2.0-5.0% w/w of the actual amphetamine content, no more than 2.0-4.0% w/w of the actual amphetamine content, no more than 5.0% w/w of the actual amphetamine content, no more than 4.0% w/w of the actual amphetamine content, no more than 3.0% w/w of the actual amphetamine content, no more than 2.0% w/w of the actual amphetamine content, or of from 0.1%-5.0% w/w, from 0.2%-5.0% w/w, from 0.3%-5.0% w/w, from 0.4%-5.0% w/w, or from 0.5%-5.0% w/w, or from 0.1%-4.0% w/w, from 0.2%-4.0% w/w, from 0.3%-4.0% w/w, from 0.4%-4.0% w/w, or from 0.5%-4.0% w/w, from 0.1%-3.0% w/w, from 0.2%-3.0% w/w, from 0.3%-3.0% w/w, from 0.4%-3.0% w/w, or from 0.5%-3.0% w/w, or from 0.1%-2.0% w/w, from 0.2%-2.0% w/w, from 0.3%-2.0% w/w, from 0.4%-2.0% w/w, or from 0.5%-2.0% w/w of the actual amphetamine content.

In some embodiments, at the time of manufacture the drug-containing polymer matrix has an amphetacarbamate content of no more than 2.0-5.0% w/w or no more than 2.0-4.0% w/w of the target amphetamine content, and, after storage for six months at ambient conditions in a sealed pouch that is substantially impervious to carbon dioxide, the drug-containing polymer matrix has an amphetacarbamate content of no more than 5.0% w/w of the target amphetamine content.

In accordance with any embodiments, the drug-containing polymer matrix may have a target amphetamine content at the time of manufacture or actual amphetamine content selected from 5% w/w dry, 10% w/w dry, 15% w/w dry, or 20% w/w dry, based on the dry weight of the polymer matrix, such as 10% w/w dry, 15% w/w dry, or 20% w/w dry, including 15% w/w dry. In specific embodiments, the drug-containing polymer matrix has a target amphetamine content at the time of manufacture or actual amphetamine content of about 15% w/w, including 15% w/w. Additionally or alternatively, in accordance with any embodiments, the drug-containing polymer matrix may have a target amphetamine content at the time of manufacture or actual amphetamine content of from about 5 mg to about 30 mg per unit dosage form; about 5 mg, about 10 mg, about 15 mg, about 20 mg, about 25 mg, or about 30 mg per unit dosage form; 5 mg, 10 mg, 15 mg, 20 mg, 25 mg, or 30 mg per unit dosage form. Additionally or alternatively, in accordance with any embodiments, the drug-containing polymer matrix may have a target amphetamine content at the time of manufacture or actual amphetamine content of from about 0.50 mg/cm$^2$ to about 2.0 mg/cm$^2$ of the active surface area of the drug-containing polymer matrix; or about 1.0 mg/cm$^2$, including about 1.05 mg/cm$^2$, of the active surface area of the drug-containing polymer matrix.

In accordance with any embodiments, the amphetamine may be or comprise d-amphetamine. In accordance with any embodiments, the amphetacarbamate may be or comprise d-amphetamine carbamate. In accordance with any embodiments, the amphetamine may be or comprise l-amphetamine. In accordance with any embodiments, the amphetacarbamate may be or comprise l-amphetacarbamate.

In accordance with any embodiments, the drug-containing polymer matrix may be substantially free of visible crystals of amphetamine carbamate.

In accordance with any embodiments, the drug-containing polymer matrix may have a shear adhesion less than that of a comparator drug-containing polymer matrix layer having the same polymer matrix components but a higher amphetacarbamate content, when assessed by the same shear adhesion test.

In accordance with any embodiments, the drug-containing polymer matrix may have a peel force greater than that of a comparator drug-containing polymer matrix layer having the same polymer matrix components but a higher amphetacarbamate content, when assessed by the same peel adhesion test.

In specific embodiments of any of the foregoing compositions or methods, the pressure-sensitive adhesive polymer component of the drug-containing polymer matrix consists of one or more non-functional acrylic polymers free of vinyl acetate moieties.

In specific embodiments of any of the foregoing compositions or methods, the pressure-sensitive adhesive polymer component of the drug-containing polymer matrix consists of one or more non-functional acrylic polymers free of vinyl acetate moieties, including at least one acrylic polymer polymerized from monomers that include (i) a soft acrylic monomer having a glass transition temperature ($T_g$) from −70° C. to −10° C. in an amount from 20-70% by weight of the polymer; and (ii) a hard acrylic monomer having a $T_g$ from −5° C. to 120° C. in an amount from 30-80% by weight of the polymer. In specific embodiments, (i) the soft acrylic monomer one or more is selected from 2-ethyl hexyl acrylate, isobutyl acrylate, ethyl acrylate, butyl acrylate, dodecyl methacrylate, 2-ethylhexyl methacrylate, 2-ethoxyethyl acrylate, isopropyl acrylate, and 2-methoxyethyl acrylate, and (ii) the hard acrylic monomer is one or more selected from methacrylate, N-butyl acrylate, acrylic acid, butyl methacrylate, ethyl methacrylate, methyl methacrylate, hexyl methacrylate, and methyl acrylate. In specific embodiments, the pressure-sensitive adhesive polymer component of the drug-containing polymer matrix consists of one or more non-functional acrylic polymers free of vinyl acetate moieties polymerized from monomers that consist of monomers selected from said soft and hard acrylic monomers (i) and (ii).

Also provided are amphetamine transdermal drug delivery systems comprising a transdermal amphetamine composition as described herein, optionally further including a backing layer, further optionally including a release liner.

Also provided are transdermal amphetamine compositions with a low amphetacarbamate content, prepared by any method disclosed herein, as well as amphetamine transdermal drug delivery systems comprising such a transdermal amphetamine composition, optionally further including a backing layer, further optionally including a release liner.

Also provided are methods of transdermally delivering amphetamine, comprising topically applying to a skin surface of a subject in need thereof, an amphetamine transdermal drug delivery system as described herein, including an amphetamine transdermal drug delivery system prepared as described herein.

Also provided are amphetamine transdermal drug delivery systems as described herein for use in transdermally delivering amphetamine to a subject in need thereof, or for treating attention deficit disorder (ADD), attention deficit hyperactivity disorder (ADHD), narcolepsy, or binge eating disorder in a subject in need thereof.

Also provided are uses of amphetamine in the preparation of a medicament for transdermally delivering amphetamine to a subject in need thereof, or for treating attention deficit disorder (ADD), attention deficit hyperactivity disorder (ADHD), narcolepsy, or binge eating disorder in a subject in need thereof, wherein the medicament is in the form of a transdermal drug delivery system as described herein.

BRIEF DESCRIPTION OF THE DRAWINGS

FIG. 2A illustrates the overall reaction scheme; FIG. 2B illustrates intermediate steps.

DETAILED DESCRIPTION

Figure 1:
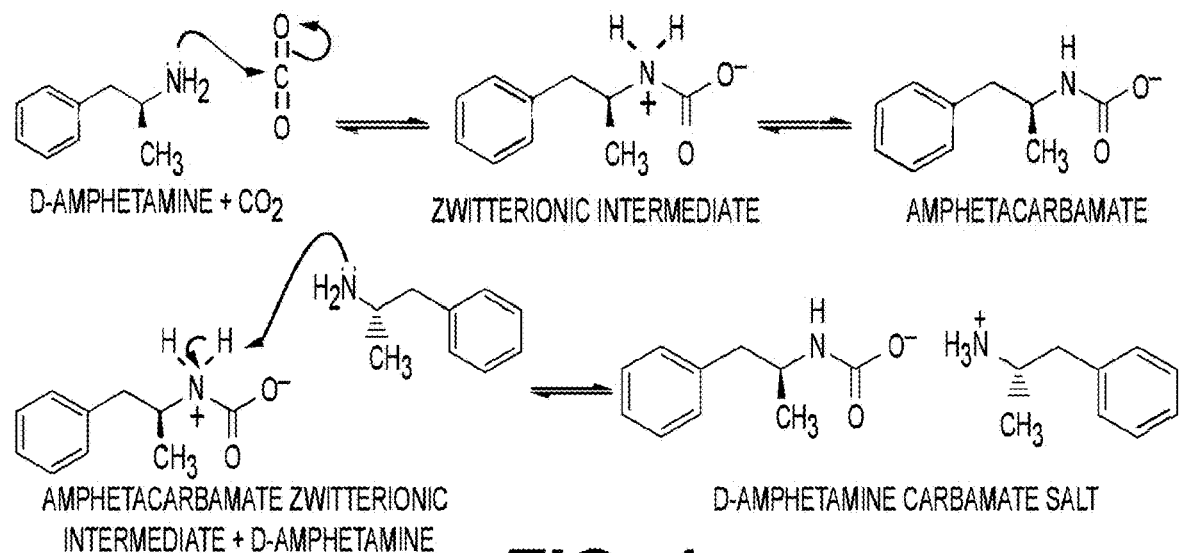
FIG. 1 illustrates a reaction scheme for the reaction of d-amphetamine with carbon dioxide to form d-amphetacarbamate which associates with ionized amphetamine (amphetammonium) to form d-amphetamine carbamate (d-amphetammonium-d-amphetacarbamate).

Described herein are transdermal amphetamine compositions, amphetamine transdermal delivery systems, methods using them for transdermal delivery of amphetamine, and methods of making the compositions and systems. The transdermal amphetamine compositions are in a flexible, finite form and comprise a drug-containing polymer matrix that includes amphetamine or a pharmaceutically acceptable salt thereof in a pressure-sensitive adhesive polymer matrix. The amphetamine transdermal delivery systems comprise (i) a drug-containing polymer matrix layer as described herein and (ii) a backing layer. The present disclosure addresses problems with transdermal amphetamine compositions that were not heretofore known in the art, including the determination that transdermal amphetamine compositions are susceptible to the formation of crystals of a newly identified salt, amphetamine carbamate, in the drug-containing polymer matrix. The present disclosure provides methods for controlling (reducing) the formation of amphetamine carbamate in transdermal amphetamine compositions, and also provides compositions and transdermal delivery systems with low levels of amphetamine carbamate, as well as methods using them to provide transdermal delivery of amphetamine.

Definitions

Technical and scientific terms used herein have the meanings commonly understood by one of ordinary skill in the art to which the present invention pertains, unless otherwise defined. Reference is made herein to various methodologies known to those of ordinary skill in the art. Except where otherwise noted or described as part of the present disclosure, any suitable materials and/or methods known to those of ordinary skill in the art can be utilized in carrying out the present invention. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than 1% by weight, based on the total weight of the composition at issue, of the excluded component(s). In some embodiments, a composition "substantially free of" excluded component(s) may be prepared without the excluded component(s), but a small amount of excluded component(s) may be present as contaminant(s), by-product(s), degradation product(s), etc.

As used herein "subject" denotes any mammal in need of drug therapy, including humans. For example, a subject may be suffering from or at risk of developing a condition that can be treated or prevented with amphetamine (such as ADD or narcolepsy), or may be taking amphetamine for other purposes.

As used herein, the terms "topical" and "topically" mean application to a skin surface of a mammal, while the terms "transdermal" and "transdermally" connote passage through the skin into systemic circulation. Thus, the compositions and systems described herein may be applied topically to a skin surface of a subject to achieve transdermal delivery of amphetamine.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

The transdermal amphetamine compositions described herein are in a "flexible, finite form." As used herein, the phrase "flexible, finite form" means a substantially solid form capable of conforming to a surface with which it comes into contact, and capable of maintaining contact so as to facilitate topical application, such as a film or patch. The transdermal amphetamine compositions described herein comprise a drug-containing polymer matrix that releases amphetamine upon application to the skin.

As used herein, the term "transdermal delivery system" refers to transdermal amphetamine compositions described herein that include a backing layer in addition to the drug-containing polymer matrix layer. Transdermal delivery systems per se are known in the art and commercially available, and often referred to as transdermal "patches."

As used herein, "active surface area" means the surface area of the drug-containing polymer matrix of the transdermal composition or transdermal delivery system.

The transdermal delivery systems may include a release liner in addition to a drug-containing polymer matrix layer and backing layer. When present, a release liner is removed prior to use, i.e., prior to application to a skin surface of a subject.

As used herein, "drug-containing polymer matrix" refers to a polymer composition which contains one or more drugs, such as amphetamine, and a polymer, such as a pressure-sensitive adhesive polymer. As used herein, the term "pressure-sensitive adhesive" refers to a viscoelastic material which adheres instantaneously to most substrates with the application of very slight pressure and remains tacky. A polymer is a pressure-sensitive adhesive polymer if it has the properties of a pressure-sensitive adhesive per se. Other polymers may function as a pressure-sensitive adhesive by admixture with one or more tackifiers, plasticizers, cross-linking agents, and/or other excipients. Thus, in some embodiments, the polymer matrix comprises a pressure-sensitive adhesive polymer and, optionally, one or more tackifiers, plasticizers, cross-linking agents, and/or other excipients. Additionally or alternatively, in some embodiments the polymer matrix comprises a polymer that functions as a pressure-sensitive adhesive by admixture with one or more tackifiers, plasticizers, cross-linking agents, and/or other excipients. In any embodiments, the polymer matrix may include one polymer or a mixture of different polymers.

The polymer matrix may be a pressure-sensitive adhesive at room temperature and exhibits desirable physical properties, such as good adherence to skin, ability to be peeled or otherwise removed without substantial trauma to the skin, retention of tack with aging, etc. The polymer matrix may have a glass transition temperature ($T_g$), measured using a differential scanning calorimeter, of between about −70° C. and about 0° C.

The compositions in flexible, finite form or transdermal delivery systems may be "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin.

Amphetamine

Amphetamine (alpha-methylphenethylamine) is a chiral drug. The solid oral dosage form ADDERALL® XR includes several different amphetamine salts, including amphetamine sulfate, amphetamine saccharate, and amphetamine aspartate monohydrate, in an overall ratio of d-amphetamine to l-amphetamine of 3:1. The solid oral dosage form VYVANSE® includes lisdexamfetamine, which is a prodrug of amphetamine. The compositions described herein may be formulated with amphetamine free base (d-amphetamine, l-amphetamine, or a mixture thereof in any relative amounts), or any pharmaceutically acceptable salt of amphetamine, or any prodrug thereof, or any combinations thereof, and with any isomeric content, and any combinations thereof In specific embodiments, the transdermal compositions described herein are formulated with d-amphetamine free base. In some embodiments, the amphetamine used to prepare the transdermal compositions described herein (referred to as the "active pharmaceutical ingredient" or "API") consists essentially of d-amphetamine, such as having a d-amphetamine content of at least 99% (w/w) and containing no more than 1% (w/w) l-amphetamine. In further specific embodiments, the API used to prepare the transdermal compositions described herein consists of d-amphetamine.

For the sake of convenience, in the discussion that follows, "amphetamine" is used to refer to d-amphetamine free base, but it is to be understood that the methods and compositions described herein can be practiced with other forms of amphetamine, including l-amphetamine free base, mixtures of d-amphetamine free base and l-amphetamine free base, pharmaceutically acceptable salts of amphetamine, prodrugs of amphetamine, and mixtures of any two or more thereof, e.g., one or more of d-amphetamine free base and l-amphetamine free base, one or more pharmaceutically acceptable salts of amphetamine, and one or more prodrugs of amphetamine.

Amphetamine Carbamate

The subject matter of the present disclosure stems from the surprising and unexpected determination that transdermal amphetamine compositions are susceptible to the formation of crystals of amphetamine carbamate in the drug-containing polymer matrix. Neither this problem, nor the existence or identity of amphetamine carbamate per se were known. Rather, amphetamine carbamate was identified and characterized by analyzing crystals isolated from drug-containing polymer matrices of transdermal amphetamine compositions. Additionally, neither the existence or identity of amphetacarbamate per se were known. Rather, amphetacarbamate was identified during the work done to identify and characterize amphetamine carbamate.

The IUPAC name for d-amphetamine carbamate (a salt) is (S)-1-phenylpropan-2-ammonium-(S)-(1-phenylpropan-2-yl)carbamate. The IUPAC name for l-amphetamine carbamate (a salt) is (R)-1-phenylpropan-2-ammonium-(R)-(1-phenylpropan-2-yl)carbamate. The salt has the chemical formula $C_{19}H_{26}N_2O_2$ with a molecular weight of 314.43 g/mol. Its chemical structure is set forth in FIG. 1, which illustrates d-amphetamine carbamate. As illustrated in FIG. 1, while not wanting to be bound by theory, it is believed that d-amphetamine reacts with carbon dioxide (e.g., atmospheric carbon dioxide) to form amphetacarbamate which combines with ionized amphetamine (amphetammonium) to form the crystalline material d-amphetamine carbamate. The proposed reaction pathway is set forth in FIG. 1. A parallel reaction occurs with l-amphetamine, to form l-amphetacarbamate and l-amphetamine carbamate.

The IUPAC name for d-amphetacarbamate is (S)-(1-phenylpropan-2-yl)carbamate. The IUPAC name for l-amphetacarbamate is (R)-(1-phenylpropan-2-yl)carbamate. Either isomer has the chemical formula $C_{10}H_{12}NO_2^-$ and a molecular weight of 178.21. Its chemical structure is set forth in FIG. 1, which depicts d-amphetacarbamate.

Figure 9:
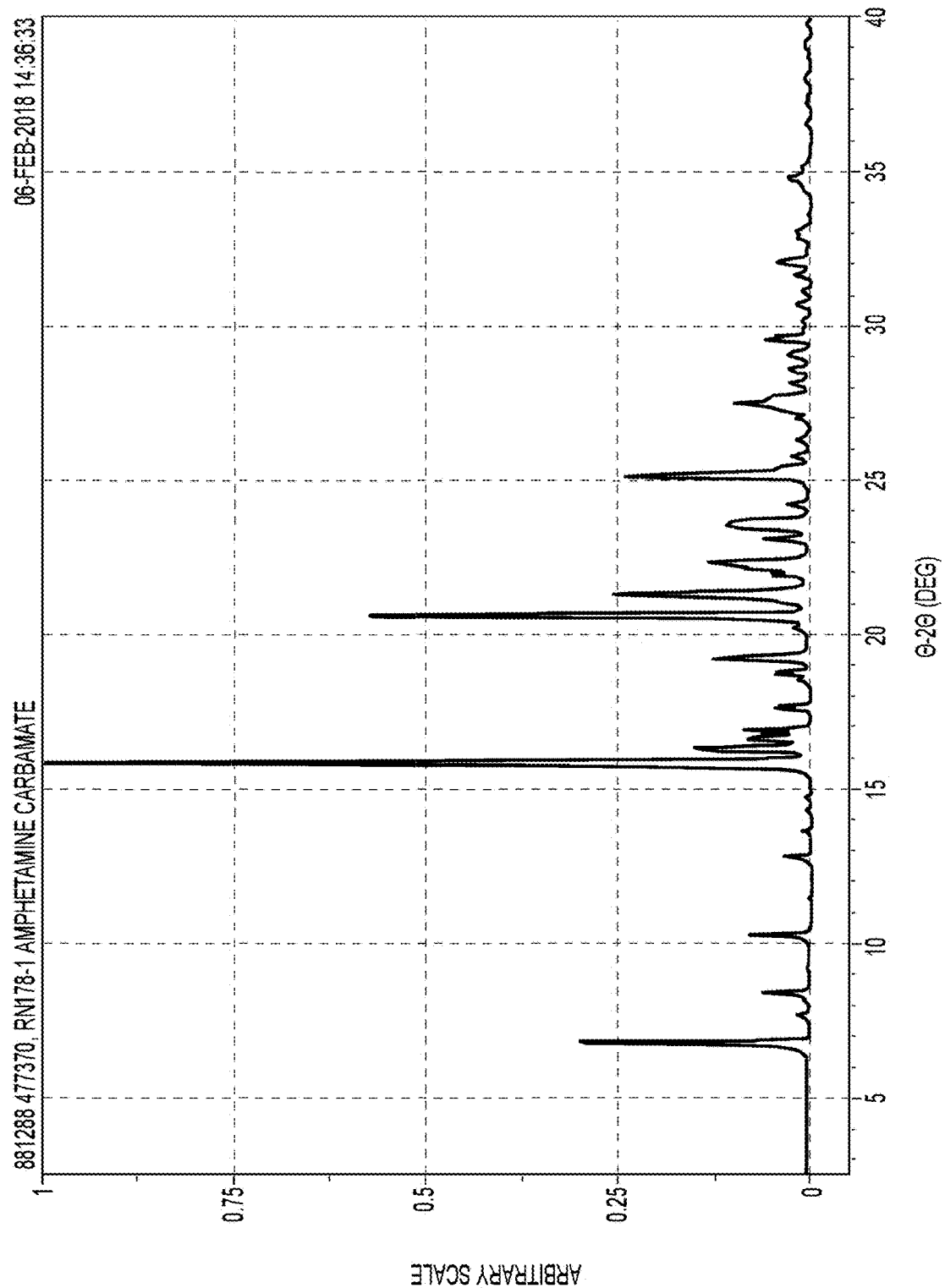
FIG. 9 sets forth a measured x-ray powder diffraction pattern for synthesized crystalline amphetamine carbamate.
Figure 10:
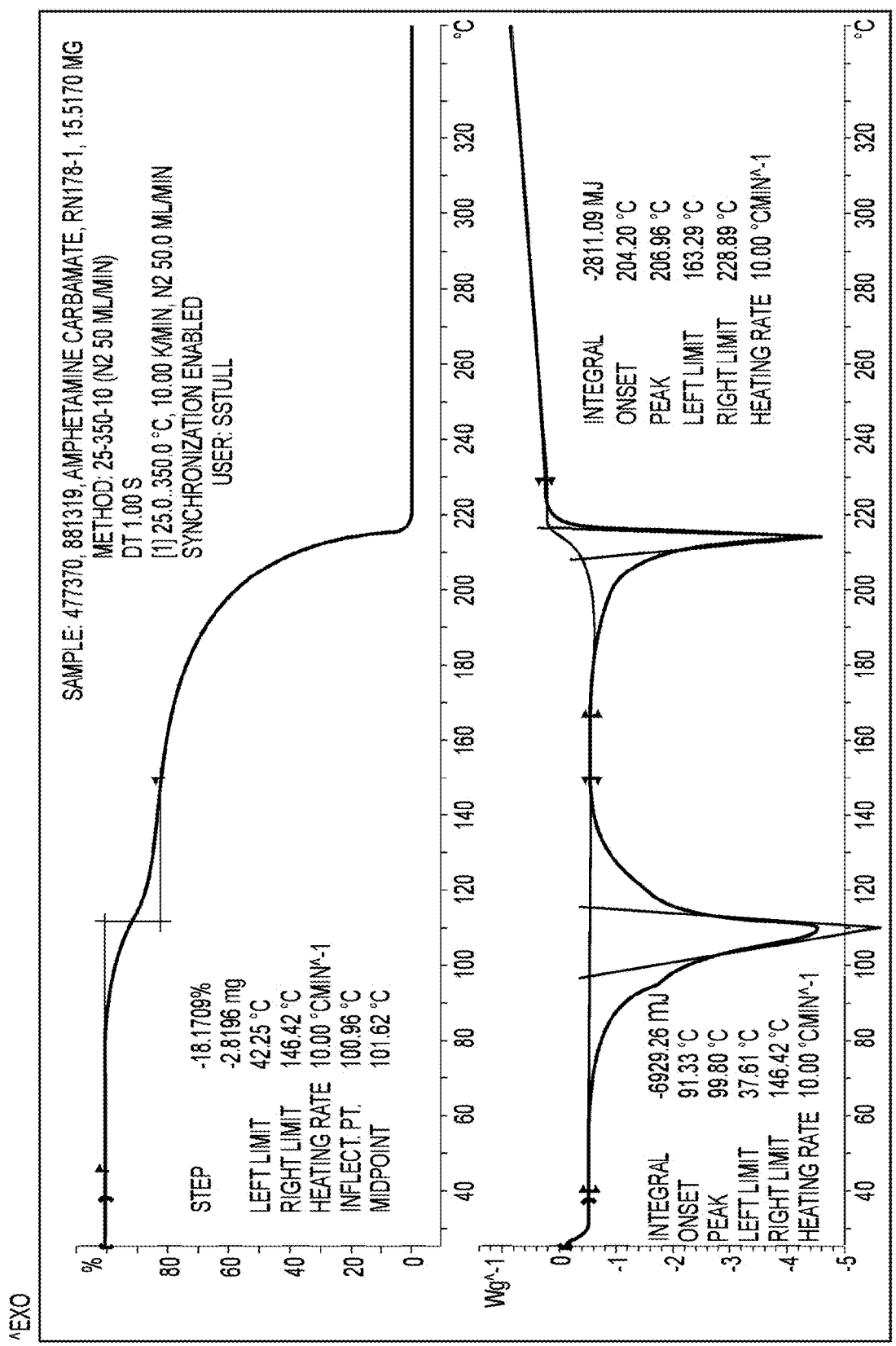
FIG. 10 sets forth a TGA/DSC thermogram of the synthesized amphetamine carbamate.

FIGS. 3-10 set forth characterizing data for d-amphetamine carbamate, including results of high resolution mass spectrometry (MS) analysis (FIG. 3) performed in negative ion mode (top panel) and positive ion mode (bottom panel); $^1H$ NMR spectral analysis (FIG. 4), $^{13}C$ NMR spectral analysis (FIG. 5), single crystal powder x-ray diffraction analysis (FIG. 6), a packing diagram for crystalline d-amphetamine carbamate viewed along the crystallographic b axis (FIG. 7), a calculated x-ray powder diffraction pattern (FIG. 8), a measured x-ray powder diffraction pattern for synthesized crystalline d-amphetamine carbamate (FIG. 9), and a TGA/DSC thermogram of the synthesized d-amphetamine carbamate (FIG. 10). Elemental analysis also was performed and consistent with the chemical structure set forth in FIG. 1. The calculated x-ray powder diffraction pattern generated from single-crystal data (FIG. 8) and the x-ray powder diffraction pattern of the synthesized d-amphetamine carbamate as shown in FIG. 9 contain different peaks, which suggests that there may be different polymorphs of the amphetamine carbamate salt. The present disclosure includes all polymorphic crystalline forms.

Without wanting to be bound by theory, it is believed that any amphetacarbamate present in a drug-containing polymer matrix will be associated with ionized amphetamine (amphetammonium) present in the polymer matrix, such that the species present is amphetamine carbamate (amphetammonium-amphetacarbamate). Nevertheless, we have chosen to define amphetamine carbamate content with reference to amphetacarbamate content. This also is convenient because the stoichiometric ratio between amphetamine and amphetacarbamate in the reactions at issue (as presently understood and illustrated in FIG. 1) is 1:1. Thus, in the discussion that follows, amphetacarbamate content is discussed and quantitated, even though the species present in a dry drug-containing polymer matrix (e.g., as made, stored, sold, offered for sale or used) may be more accurately described as amphetamine carbamate (amphetammonium-amphetacarbamate).

Transdermal Amphetamine Compositions with Low Levels of Carbamate

The transdermal amphetamine compositions and amphetamine transdermal delivery systems disclosed herein have low levels of amphetamine carbamate and low levels of amphetacarbamate. The amphetacarbamate content of a drug-containing polymer matrix layer can be determined as discussed in more detail below and illustrated in Example 1 below, and described in more detail in U.S. provisional application 63/134,852, filed Jan. 7, 2021, by Applicant Noven Pharmaceuticals, Inc., entitled "AMPHETAMINE CARBAMATE COMPOUNDS AND METHODS," the entire contents of which are incorporated herein by reference in their entirety, and the PCT application claiming priority thereto.

The transdermal amphetamine compositions described herein include a therapeutically effective amount of amphetamine and/or pharmaceutically acceptable salt(s) and/or prodrug(s) thereof. Generally, the actual or target amphetamine content is from about 1% to about 50%, including from about 1% to about 40% or from about 1% to about 30% or from about 1% to about 20%, such as from about 10% to about 30% or from about 10% to about 20%, including from about 15% to about 25%, including 1%, 5%, 10%, 15%, 20%, 25, or 30%, or any amount or range between any of these exemplary amounts, all by weight based on the total dry weight of the drug-containing polymer matrix (% w/w dry). In a typical product line, the actual amphetamine content of given transdermal amphetamine composition or amphetamine transdermal delivery system is within +10% of the applicable target amphetamine content. As used herein, the term "target amphetamine content" means the intended amphetamine content of the final product, such as the amount that would provide the "label claim" amount of amphetamine in a final dosage form (e.g., the amount that would be indicated as present on final product labeling, such as the FDA-approved product label).

In specific embodiments, the drug-containing polymer matrix has or is formulated to achieve a target amphetamine content of about 15% w/w dry in the finished product. In other specific embodiments, the drug-containing polymer matrix has or is formulated to achieve a target amphetamine content of about 5% w/w dry in the finished product. In other specific embodiments, the drug-containing polymer matrix has or is formulated to achieve a target amphetamine content of about 10% w/w dry in the finished product. In other specific embodiments, the drug-containing polymer matrix has or is formulated to achieve a target amphetamine content of about 20% w/w dry in the finished product. The phrase "is formulated to achieve a target amphetamine content of . . . in the finished product" means that the stated amount (or % wt/wt) is the target amount (or % wt/wt) of amphetamine for the finished product, and is based on the assumption that the amphetamine used is 100% amphetamine, e.g., is based on the assumption that the amphetamine API is 100% amphetamine, and not accounting for any trace impurities or degradation products in the API, including not accounting for any amphetacarbamate or amphetamine carbamate that may be present in the API. The phrase "is formulated to achieve a target amphetamine content of . . . in the finished product" also means that the amount of API used in the manufacturing process is sufficient to account for loss in API (e.g., loss of amphetamine and amphetamine-related species) during the manufacturing process. As discussed in more detail below, because amphetamine is a volatile drug, some API is lost during the manufacturing process. Thus, as also discussed in more detail below, a manufacturing overage of API is used at the start of the manufacturing process in order to obtain a product with the target amount of amphetamine in the finished product.

Additionally or alternatively, target amphetamine content may be described with reference to the amphetamine content of a unit dosage form (e.g., a "patch"), sometimes referred to as the "potency" of the unit dosage form or the "label claim" amount) (e.g., the amount that would be indicated as present on final product labeling, such as the FDA-approved product label). Thus, in accordance with any of the embodiments described herein, a transdermal amphetamine composition or amphetamine transdermal delivery system as described herein may have or be formulated to achieve a target amphetamine content of from about 5 mg to about 30 mg of amphetamine free base per unit dosage form (e.g., per patch), or an equivalent amount of a pharmaceutically acceptable salt or prodrug thereof, including about 5 mg, about 10 mg, about 15 mg, about 20 mg, about 25 mg, or about 30 mg of amphetamine free base or equivalent, such as 5 mg, 10 mg, 15 mg, 20 mg, 25 mg, or 30 mg amphetamine free base or equivalent. In a typical product line, the actual amphetamine content of given unit dosage form is within +10% of the applicable target amphetamine content. The potency of a unit dosage form depends on the relative amount (% w/w dry) of amphetamine in the drug-containing polymer matrix, the coat weight of the drug-containing polymer matrix (mg/cm$^2$ dry) and the size of the active surface area (cm$^2$).

Additionally or alternatively, target amphetamine content may be described with reference to the amount of amphetamine per unit area of the active surface area of the drug-containing polymer matrix (e.g., mg/cm$^2$ of the active surface area). The amphetamine content per unit area depends on both the relative amount (% w/w dry) of amphetamine in the drug-containing polymer matrix and the coat weight of the drug-containing polymer matrix (mg/cm$^2$ dry). As discussed in more detail below, a typical coat weight for a drug-containing polymer matrix of a monolithic transdermal amphetamine composition or amphetamine transdermal delivery system ranges from about 3 mg/cm$^2$ to about 10 mg/cm$^2$, or from about 3 mg/cm$^2$ to about 15 mg/cm$^2$. In specific embodiments, the actual or target amphetamine content is from about 0.5 0 mg/cm$^2$ to about 3.0 mg/cm$^2$ of the active surface area of the drug-containing polymer matrix, such as about 1.0 mg/cm$^2$ of the active surface area, including about 1.05 mg/cm$^2$ of the active surface area. Other exemplary actual or target amounts include about 0.75 mg/cm$^2$, about 0.8 mg/cm$^2$, about 0.9 mg/cm$^2$, about 1.0 mg/cm$^2$, about 1.05 mg/cm$^2$, about 1.1 mg/cm$^2$, about 1.2 mg/cm$^2$, about 1.25 mg/cm$^2$, about 1.5 mg/cm$^2$, about 2.0 mg/cm$^2$, about 2.5 mg/cm$^2$, and about 3.0 mg/cm$^2$, including 0.75 mg/cm$^2$, 0.8 mg/cm$^2$, 0.9 mg/cm$^2$, 1.0 mg/cm$^2$, 1.05 mg/cm$^2$, 1.1 mg/cm$^2$, 1.2 mg/cm$^2$, and 1.25 mg/cm$^2$, 1.5 mg/cm$^2$, 2.0 mg/cm$^2$, 2.5 mg/cm$^2$, and 3.0 mg/cm$^2$. In a typical product line, the actual amphetamine content per unit area of the active surface area is within +10% of the applicable target amphetamine content.

Amphetacarbamate Content Relative to Dry Weight of Drug-Containing Polymer Matrix In some embodiments, the drug-containing polymer matrix of a transdermal amphetamine composition or amphetamine transdermal delivery system as disclosed herein has an amphetacarbamate content that is no more than 1.0% w/w, based on the total dry weight of the drug-containing polymer matrix ("% w/w dry"). That is, in accordance with some embodiments, the transdermal amphetamine compositions disclosed herein have a drug-containing polymer matrix layer that has an amphetacarbamate content of no more than 1.0% w/w dry, no more than 0.9% w/w dry, no more than 0.8% w/w dry, no more than 0.75% w/w dry, no more than 0.7% w/w dry, no more than 0.6% w/w dry, no more than 0.5% w/w dry, no more than 0.4% w/w dry, no more than 0.3% w/w dry, no more than 0.2% w/w dry, no more than 0.1% w/w dry, no more than 0.05% w/w dry, or no more than 0.01% w/w dry. Thus, in accordance with some embodiments, the drug-containing polymer matrix layer has an amphetacarbamate content of 0.01%-1.0.% w/w dry, 0.01%-0.9% w/w dry, 0.01%-0.8% w/w dry, 0.01%-0.7% w/w dry, 0.01%-0.75% w/w dry, 0.01-0.6% w/w dry, 0.01%-0.5% w/w dry, 0.01-0.4% w/w dry, 0.01%-0.3% w/w dry, 0.01-0.2% w/w dry, 0.01-1.0% w/w dry, or from 0.10%-0.8.% w/w dry, 0.01%-0.75% w/w dry, 0.10%-0.7% w/w dry, 0.1-0.6% w/w dry, 0.1%-0.5% w/w dry, 0.1-0.4% w/w dry, 0.1%-0.3% w/w dry, 0.1-0.2% w/w dry, or 0.1-1.0% w/w dry.

In specific embodiments, the amphetacarbamate content of the drug-containing polymer matrix is no more than 0.9% w/w dry, including from 0.01-0.9% w/w dry or from 0.1-0.9% w/w dry. In further specific embodiments, the amphetacarbamate content of the drug-containing polymer matrix is no more than 0.75% w/w dry, including from 0.01-0.75% w/w dry or from 0.1-0.75% w/w dry. In further specific embodiments, the amphetacarbamate content of the drug-containing polymer matrix is no more than 0.6% w/w dry, including from 0.01-0.6% w/w dry or from 0.1-0.6% w/w dry.

In accordance with any of these embodiments, the drug-containing polymer matrix may have any amphetamine content discussed above and/or any target amphetamine content discussed above. In specific embodiments, the drug-containing polymer matrix has an actual amphetamine content or target amphetamine content at the time of manufacture of 10% w/w dry. In other specific embodiments, the drug-containing polymer matrix has an actual amphetamine content or target amphetamine content at the time of manufacture of 15% w/w dry. In other specific embodiments, the drug-containing polymer matrix has an actual amphetamine content or target amphetamine content at the time of manufacture of 20% w/w dry. Additionally or alternatively, the drug-containing polymer matrix may have an actual amphetamine content or target amphetamine content at the time of manufacture of from about 5 mg to about 30 mg per unit dosage form (e.g., per patch), including about 5 mg, about 10 mg, about 15 mg, about 20 mg, about 25 mg, or about 30 mg amphetamine, such as 5 mg, 10 mg, 15 mg, 20 mg, 25 mg, or 30 mg amphetamine. Additionally or alternatively, the drug-containing polymer matrix may have an actual amphetamine content or target amphetamine content at the time of manufacture of from about 0.5 0 mg/cm$^2$ to about 3.0 mg/cm$^2$ of the active surface area of the drug-containing polymer matrix at the time of manufacture, such as about 1.0 mg/cm$^2$ or 1.05 mg/cm$^2$ of the active surface area.

Amphetacarbamate Content Relative to Amphetamine Content

Additionally or alternatively, in some embodiments, the drug-containing polymer matrix of transdermal amphetamine composition or amphetamine transdermal delivery system as disclosed herein has an amphetacarbamate content that is no more than 5.0% w/w, no more than 4.0% w/w, no more than 3.0% w/w, no more than 2.0% w/w, or no more than 1.0% w/w of the target amphetamine content at the time of manufacture. Thus, in accordance with some embodiments, the drug-containing polymer matrix layer of the finished product has an amphetacarbamate content that is from 0.1-5.0% w/w, from 0.1-4.0% w/w, from 0.1%-3.0% w/w, from 0.1-2.0% w/w, or from 0.1-1.0% w/w, or less, of the target amphetamine content at the time of manufacture, or from 0.2-5.0% w/w, from 0.2-4.0% w/w, from 0.2%-3.0% w/w, from 0.2-2.0% w/w, or from 0.2-1.0% w/w, or less, of the target amphetamine content at the time of manufacture, or from 0.3-5.0% w/w, from 0.3-4.0% w/w, from 0.3-3.0% w/w, from 0.3-2.0% w/w, from 0.3-1.0% w/w, or less, of the target amphetamine content at the time of manufacture, or from 0.4-5.0% w/w, from 0.4-4.0% w/w, from 0.4-3.0% w/w, from 0.4-2.0% w/w, from 0.4-1.0% w/w, or less, of the target amphetamine content at the time of manufacture, or from 0.5-5.0% w/w, from 0.5-4.0% w/w, from 0.5%-3.0% w/w, from 0.5%-2.0% w/w, or from 0.5%-1.0% w/w, or less, of the target amphetamine content at the time of manufacture.

In specific embodiments, at the time of manufacture, the amphetacarbamate content of the drug-containing polymer matrix is no more than 2.0-5.0% w/w or no more than 2.0-4.0% w/w of the target amphetamine content, including no more than 3.0-4.0% w/w of the target amphetamine content, including no more than 4.0% w/w of the target amphetamine content, no more than 3.0% w/w of the target amphetamine content, or no more than 2.0% w/w of the target amphetamine content, including from 0.1%-5.0% w/w, from 0.2%-5.0% w/w, from 0.3%-5.0% w/w, from 0.4%-5.0% w/w, or from 0.5%-5.0% w/w, or from 0.1%-4.0% w/w, or from 0.2%-4.0% w/w, or from 0.3%-4.0% w/w, or from 0.4%-4.0% w/w, or from 0.5%-4.0% w/w, from 0.1%-3.0% w/w, or from 0.2%-3.0% w/w, or from 0.3%-3.0% w/w, or from 0.4%-3.0% w/w, or from 0.5%-3.0% w/w, or from 0.1%-3.0% w/w, from 0.2%-2.0% w/w, from 0.3%-2.0% w/w, or from 0.4%-2.0% w/w, or from 0.5%-2.0% w/w of the target amphetamine content.

At the time of manufacture, the amphetacarbamate content of the drug-containing polymer matrix may be no more than about 3.0% w/w of the target amphetamine content of the polymer matrix, including no more than 3.0% w/w of the target amphetamine content of the polymer matrix. At the time of manufacture, the amphetacarbamate content of the drug-containing polymer matrix may be no more than about 5.0% w/w of the target amphetamine content of the polymer matrix, or no more than about 4.0% w/w of the target amphetamine content of the polymer matrix, including no more than 5.0% w/w of the target amphetamine content of the polymer matrix or no more than 4.0% w/w of the target amphetamine content of the polymer matrix.

Additionally or alternatively, in some embodiments, at the time of manufacture the drug-containing polymer matrix of transdermal amphetamine composition or amphetamine transdermal delivery system as disclosed herein has an amphetacarbamate content that is no more than 5.0% w/w, no more than 4.0% w/w, no more than 3.0% w/w, no more than 2.0% w/w, or no more than 1.0% w/w of the actual amphetamine content. Thus, in accordance with some embodiments, at the time of manufacture the drug-containing polymer matrix layer of the finished product has an amphetacarbamate content that is from 0.1-5.0% w/w, from 0.1-4.0% w/w, from 0.1%-3.0% w/w, from 0.1-2.0% w/w, or from 0.1-1.0% w/w, or less, of the actual amphetamine content, or from 0.2-5.0% w/w, from 0.2-4.0% w/w, from 0.2%-3.0% w/w, from 0.2-2.0% w/w, or from 0.2-1.0% w/w, or less, of the actual amphetamine content, or from 0.3-5.0% w/w, from 0.3-4.0% w/w, from 0.3-3.0% w/w, from 0.3-2.0% w/w, from 0.3-1.0% w/w, or less, of the actual amphetamine content, or from 0.4-5.0% w/w, from 0.4-4.0% w/w, from 0.4-3.0% w/w, from 0.4-2.0% w/w, from 0.4-1.0% w/w, or less, of the target amphetamine content at the time of manufacture, or from 0.5-5.0% w/w, from 0.5-4.0% w/w, from 0.5%-3.0% w/w, from 0.5%-2.0% w/w, or from 0.5%-1.0% w/w, or less, of the actual amphetamine content.

In specific embodiments, at the time of manufacture the amphetacarbamate content of the drug-containing polymer matrix is no more than 2.0-5.0% w/w of the actual amphetamine content, or no more than 2.0-4.0% w/w of the actual amphetamine content, including no more than 5.0% w/w of the actual amphetamine content, or no more than 4.0% of the actual amphetamine content, no more than 3.0% of the actual amphetamine content, or no more than 2.0% of the actual amphetamine content, including from 0.1%-5.0% w/w, or from 0.2%-5.0% w/w, or from 0.3%-5.0% w/w, or from 0.4%-5.0% w/w, or from 0.5%-5.0% w/w, or from 0.1%-4.0% w/w, or from 0.2%-4.0% w/w, or from 0.3%-4.0% w/w, or from 0.4%-4.0% w/w, or from 0.5%-4.0% w/w, or from 0.1%-3.0% w/w, or from 0.2%-3.0% w/w, or from 0.3%-3.0% w/w, or from 0.4%-3.0% w/w, or from 0.5%-3.0% w/w, or from 0.1%-2.0% w/w, or from 0.2%-2.0% w/w, or from 0.3%-2.0% w/w, or from 0.4%-2.0% w/w, or from 0.5%-2.0% w/w of the actual amphetamine content. In some embodiments, at the time of manufacture, the amphetacarbamate content of the drug-containing polymer matrix is no more than about 3.0% w/w of the actual amphetamine content of the polymer matrix, including no more than 3.0% w/w of the actual amphetamine content of the polymer matrix. In some embodiments, at the time of manufacture, the amphetacarbamate content of the drug-containing polymer matrix is no more than about 4.0% w/w of the actual amphetamine content of the polymer matrix, including no more than 4.0% w/w of the actual amphetamine content of the polymer matrix. In some embodiments, at the time of manufacture, the amphetacarbamate content of the drug-containing polymer matrix is no more than about 5.0% w/w of the actual amphetamine content of the polymer matrix, including no more than 5.0% w/w of the actual amphetamine content of the polymer matrix.

In accordance with any of these embodiments, the drug-containing polymer matrix may have any actual amphetamine content discussed above and/or any target amphetamine content discussed above. In specific embodiments, the drug-containing polymer matrix has an actual amphetamine content or target amphetamine content at the time of manufacture of 15% w/w dry. In other specific embodiments, the drug-containing polymer matrix has an actual amphetamine content or target amphetamine content at the time of manufacture of 10% w/w dry. In other specific embodiments, the drug-containing polymer matrix has an actual amphetamine content or target amphetamine content at the time of manufacture of 20% w/w dry. In specific embodiments, the drug-containing polymer matrix has an actual amphetamine content or target amphetamine content at the time of manufacture of 5% w/w dry. Additionally or alternatively, the drug-containing polymer matrix may have an actual amphetamine content or target amphetamine content at the time of manufacture of from about 5 mg to about 30 mg per unit dosage form (e.g., per patch), including about 5 mg, about 10 mg, about 15 mg, about 20 mg, about 25 mg, or about 30 mg amphetamine, such as 5 mg, 10 mg, 15 mg, 20 mg, 25 mg, or 30 mg amphetamine. Additionally or alternatively, the drug-containing polymer matrix may have an actual amphetamine content or target amphetamine content at the time of manufacture of from about 0.5 0 mg/cm$^2$ to about 3.0 mg/cm$^2$ of the active surface area of the drug-containing polymer matrix at the time of manufacture, such as about 1.0 mg/cm$^2$ or 1.05 mg/cm$^2$ of the active surface area.

Stability Against Increased Amphetamine Carbamate Content

The transdermal amphetamine compositions and amphetamine transdermal delivery systems disclosed herein have low levels of amphetamine carbamate and low levels of amphetacarbamate at the time of manufacture. It is believed that the amphetamine carbamate content of a transdermal amphetamine composition or amphetamine transdermal delivery system as described herein is stable against the formation of additional amphetamine carbamate, particularly if the composition or system is maintained under conditions that protect the amphetamine from exposure to carbon dioxide. Thus, for example, a drug-containing polymer matrix composition stored in a sealed package purged of carbon dioxide and impervious to carbon dioxide (e.g., a sealed pouch) is expected to be stable against the formation of additional amphetamine carbamate. An amphetamine transdermal delivery system, in which the drug-containing polymer matrix is protected from exposure to carbon dioxide by a backing layer and release liner, is expected to be stable against the formation of additional amphetamine carbamate without requiring further protection from carbon dioxide, e.g., without requiring special packaging or pouch material. However, there may be a risk that amphetamine present at the edge of the system could be exposed to enough carbon dioxide to form amphetamine carbamate. Thus, in some embodiments a transdermal amphetamine composition or amphetamine transdermal delivery system as disclosed herein is packaged and stored so as to limit exposure to carbon dioxide, such as in a sealed pouch that is substantially impervious to carbon dioxide, such as a sealed pouch made from a multilayer pouch stock material comprising, e.g., a polyester layer, a polyethylene layer and a foil layer, wherein the pouch is optionally purged of air/carbon dioxide prior to sealing.

As noted above, in some embodiments, at the time of manufacture the drug-containing polymer matrix has an amphetacarbamate content of no more than 2.0-5.0% w/w of the target amphetamine content, or no more than 2.0-4.0% w/w of the target amphetamine content, such as no more than 3.0% w/w of the target amphetamine content, or no more than 4.0% w/w of the target amphetamine content, or no more than 5.0% w/w of the target amphetamine content. In some embodiments, after storage at ambient conditions in a sealed pouch that is substantially impervious to carbon dioxide, the drug-containing polymer matrix has an amphetacarbamate content of no more than 3.0-8.0% w/w of the target amphetamine content, such as no more than 5.0% w/w of the target amphetamine content, or no more than 8.0% w/w of the target amphetamine content, such as after storage under such conditions for six months, one year, 18 months, or two years.

Thus, in some embodiments, provided herein are transdermal amphetamine compositions and amphetamine transdermal delivery system, wherein the drug-containing polymer matrix has an amphetacarbamate content of no more than 5.0% w/w of the target amphetamine content, including no more than 4.0% w/w of the target amphetamine content, including no more than 3.0% w/w of the target amphetamine content.

Impact of Amphetamine Carbamate Content

It was surprisingly determined that the presence of amphetamine carbamate in the drug-containing polymer matrix of an amphetamine transdermal compositions has detrimental effects on physical properties of the compositions. First, crystals of amphetamine carbamate may form in the polymer matrix. For example, it was found experimentally that a high polymer matrix amphetacarbamate/amphetamine carbamate content may lead to the formation of visible crystals of amphetamine carbamate in the polymer matrix. Additionally, in other experiments, it was found that physical properties of a transdermal amphetamine composition or amphetamine transdermal delivery system, including shear properties and peel force properties, are negatively impacted with higher polymer matrix amphetacarbamate/amphetamine carbamate content, as illustrated in the examples below. Without being limiting, it is noted that crystals of amphetamine carbamate tend to form when the amphetacarmabate content is greater than 4% of the target amphetamine content (or of the actual amphetamine content), such as when the amphetacarmabate content is about 4.5% w/w or more of the target amphetamine content (or of the actual amphetamine content), or about 5% w/w or more. Other physical properties of a transdermal amphetamine composition or amphetamine transdermal delivery system may be affected when the amphetacarmabate content is about 8% w/w or more of the target amphetamine content (or of the actual amphetamine content).

Polymer Matrix

The invention disclosed herein does not depend on the specific polymer matrix, and may be practiced with any amphetamine transdermal composition comprising a drug-containing polymer matrix comprising amphetamine in any polymer matrix. Nevertheless, for the purpose of illustration, described herein are examples of polymer matrix components suitable for transdermal amphetamine compositions.

Acrylic Polymers

In accordance with some embodiments, the drug-containing polymer matrix comprises, consists essentially of, or consists of amphetamine and at least one acrylic polymer. In this context, the phrase "consists essentially of" means that the polymer matrix is substantially free of other polymer components (e.g., substantially free of polymers other than one or more acrylic polymers) and is substantially free of skin permeation enhancers, but it may include other excipients known to be useful in transdermal compositions (such as tackifiers, plasticizers, crosslinking agents or other excipients known in the art, such as antioxidants) as long as those other excipients do not degrade the physical and/or pharmacokinetic properties of the compositions to pharmaceutically unacceptable levels.

The use of acrylic polymers in a drug-containing polymer matrix for a transdermal amphetamine composition has been described. For example, the present Applicant has described transdermal amphetamine compositions and amphetamine transdermal delivery compositions in U.S. Pat. Nos. 7,993,671; 8,632,802; 8,216,606; 9,034,370; 8,337,884; 8,187,628; 8,916,191; 8,591,941; 8,815,281; 9,155,712; 10,231,938; 9,333,263; 9,456,993; 9,474,722; 9,901,552; 10,004,696, U.S. Patent Application Publication 2015/0104495; U.S. Pat. Nos. 8,703,175; 9,295,726; U.S. Patent Application Publication 2015/0342899, the contents of each of which are hereby incorporated by reference in their entirety. Any such transdermal amphetamine compositions and amphetamine transdermal delivery compositions can be prepared in accordance with the methods described herein to obtain transdermal amphetamine compositions and amphetamine transdermal delivery compositions with low levels of amphetamine carbamate/amphetacarbamate.

In accordance with specific embodiments, the drug-containing polymer matrix may comprise, consist essentially of, or consist of amphetamine and a blend of acrylic polymers having different functionalities (e.g., different types and/or amounts of functional groups) that provides a net solubility parameter for the active agent (e.g., amphetamine). See, e.g., U.S. Pat. No. 8,187,628, the entire contents of which are hereby incorporated by reference. In accordance with specific embodiments, the polymer matrix comprises or consists of one or more non acid-functional acrylic polymers as the polymer component. Non acid-functional acrylic polymers include those formed from acrylic esters copolymerized with other monomers that do not include acid-functional groups. Non acid-functional acrylic polymers include homopolymers, copolymers, terpolymers, etc., of acrylic acids and esters. As used herein, "non acid-functional acrylic polymer" includes polymers that include monomers that have one or more amide groups.

Suitable acrylic polymers can be obtained commercially or by polymerizing or copolymerizing suitable monomers such as acrylic monomers and other polymerizable monomers. Acrylate monomers which can be used include acrylic acid, methacrylic acid, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. Examples of suitable non acid-functional acrylic polymers include those polymerized from methacrylate (methyl acrylate) monomers and 2-ethylhexyl acrylate monomers; those polymerized from methacrylate (methyl acrylate) monomers, 2-ethylhexyl acrylate monomers, and amide-group containing monomers, and, optionally, butyl acrylate monomers; and those polymerized from methyl methacrylate monomers alone or along with any one or more of the non-acid functional monomers listed above.

In some embodiments, the pressure-sensitive adhesive polymer component of the drug-containing polymer matrix consists of one or more non-functional acrylic polymers free of vinyl acetate moieties. In further specific embodiments, the pressure-sensitive adhesive polymer component of the drug-containing polymer matrix consists of one or more non-functional acrylic polymers free of vinyl acetate moieties, including at least one acrylic polymer polymerized from monomers that include (i) a soft acrylic monomer having a glass transition temperature ($T_g$) from −70° C. to −10° C. in an amount from 20-70% by weight of the polymer; and (ii) a hard acrylic monomer having a $T_g$ from −5° C. to 120° C. in an amount from 30-80% by weight of the polymer. See, e.g., U.S. Pat. Nos. 9,034,370 and 8,632,802, the entire contents of each of which are hereby incorporated by reference. In further specific embodiments, (i) the soft acrylic monomer one or more is selected from 2-ethyl hexyl acrylate, isobutyl acrylate, ethyl acrylate, butyl acrylate, dodecyl methacrylate, 2-ethylhexyl methacrylate, 2-ethoxyethyl acrylate, isopropyl acrylate, and 2-methoxyethyl acrylate, and (ii) the hard acrylic monomer is one or more selected from methacrylate, N-butyl acrylate, acrylic acid, butyl methacrylate, ethyl methacrylate, methyl methacrylate, hexyl methacrylate, and methyl acrylate. In further specific embodiments, the pressure-sensitive adhesive polymer component of the drug-containing polymer matrix consists of one or more non-functional acrylic polymers free of vinyl acetate moieties polymerized from monomers that consist of monomers selected from said soft and hard acrylic monomers (i) and (ii).

Suitable non-acid functional random acrylic polymers which are commercially available include those sold by Henkel North America under the DURO-TAK® brand name such as DURO-TAK® 87-900A, 87-901A, 87-9085, 87-9088, 87-9301A, and by Cytec Industries Inc. under the GELVA® GMS brand name, such as GELVA® GMS 3067, 3071, 3083, 3087 and 3235. Other suitable acrylic polymers are known in the art. See, e.g., the non acid-functional acrylic polymers described in Satas, "Acrylic Adhesives, HANDBOOK OF PRESSURE-SENSITIVE ADHESIVE TECHNOLOGY, 2nd ed., pp. 396-456 (D. Satas, ed.), Van Nostrand Reinhold, N. Y. (1989); "Acrylic and Methacrylic Ester Polymers," POLYMER SCIENCE AND ENGINEERING, Vol. 1, 2nd ed., pp 234-268, John Wiley & Sons, (1984).

When the acrylic polymer component includes more than one acrylic polymer, the polymers can be present in any ratio that results in a product with satisfactory physical and pharmacokinetic properties. For example, the acrylic polymer component can include from 0-100% of a first non acid-functional acrylic polymer and from 100-0% of a second non acid-functional acrylic polymer, based on the total dry weight of the acrylic component, including from about 10 to about 90%, about 15 to about 85%, about 20 to about 80%, about 25 to about 75%, about 33 to about 66%, and about 50% of the first non acid-functional acrylic polymer, and the balance being the second (or third, etc.) non acid-functional acrylic polymer(s). In specific embodiments, the acrylic polymer component includes about 80% of a first non acid-functional acrylic polymer and about 20% of a second non acid-functional acrylic polymer, based on the total polymer content.

As noted above, in some embodiments, the polymer matrices of the compositions described herein consist essentially of amphetamine or pharmaceutically acceptable salt(s) thereof and at least one acrylic polymer, although such compositions may include other non-polymer components that do not degrade the physical and/or pharmacokinetic properties of the compositions to pharmaceutically unacceptable levels. Generally, for polymer matrices that include amphetamine in an amount from about 1% to about 50%, including from about 1% to about 40% or from about 1% to about 30% or from about 1% to about 20%, such as from about 10% to about 30% or from about 10% to about 20%, including from about 15% to about 25%, including 1%, 5%, 10%, 15%, 20%, 25, or 30%, based on the total dry weight of the polymer matrix, the one or more acrylic polymers will constitute from about 50% to about 99%, including 60% to about 99%, such as from about 70% to about 99%, or from about 80% to about 99%, or from about 75% to about 85%, by weight of the polymer matrix, based on the total dry weight of the polymer matrix, with this number being adjusted to account for any excipients. In specific embodiments, the polymer matrix comprises about 85% by weight of one or more acrylic polymers, based on the total dry weight of the polymer matrix. In further specific embodiments, the polymer matrix comprises about 85% by weight of one or more non acid-functional acrylic polymers, based on the total dry weight of the polymer matrix.

Backing Layer

The compositions in flexible, finite form comprise a drug-containing polymer matrix, such as described above, and a backing layer. The backing layer is impermeable to the drug (e.g., impermeable to the amphetamine) and is adjacent one face of the drug-containing polymer matrix. (By "impermeable" to the drug is meant that no substantial amount of drug loss through the backing layer is observed) The backing layer protects the polymer matrix from the environment and prevents loss of the drug and/or release of other components to the environment during use.

The backing layer may be made from any material known to be suitable for a backing layer for a transdermal pharmaceutical compositions, including commercially available backing materials. The present Applicant has described backing layers particularly suitable for transdermal amphetamine compositions, for example in U.S. Pat. Nos. 8,591,941; 8,815,281; 9,155,712; 10,231,938; 9,456,993; 9,474,722; 9,901,552; 10,004,696, and U.S. Patent Application Publication 2015/0104495, the contents of each of which are hereby incorporated by reference in their entirety. Thus, in some embodiments that backing layer comprises a backing layer as described in any of U.S. Pat. Nos. 8,591,941; 8,815,281; 9,155,712; 10,231,938; 9,456,993; 9,474,722; 9,901,552; 10,004,696, and U.S. Patent Application Publication 2015/0104495.

In specific embodiments, the backing layer is a multi-layer backing layer, such as a multi-layer laminate, that includes a polyurethane film layer and a polyester film layer, optionally with an adhesive disposed between the two layers, wherein the adhesive may be a polyurethane adhesive. In some embodiments, the backing layer consists of a polyester film layer, a polyurethane film layer, and an adhesive disposed between the two layers. In accordance with any of these embodiments, in the context of the system as a whole, the polyurethane layer of the backing layer may be adjacent the polymer matrix. In specific embodiments, the backing layer is a multi-layer backing layer that includes a polyurethane film layer and a polyester film layer, with a polyurethane adhesive disposed between the two layers, as disclosed in U.S. Pat. Nos. 9,456,993; 9,474,722; 9,901,552; and 10,004,696, the entire contents of which are incorporated herein by reference.

Release Liner

The compositions in flexible, finite form may further comprise a release liner, typically located adjacent the opposite face of the system as the backing layer. When present, the release liner is removed from the system prior to use to expose the drug-containing polymer matrix layer prior to topical application. Materials suitable for use as release liners are well-known in the art and commercially available, such as polyester release liners, including coated polyester release liners, such as siliconized or fluoro-coated polyester release liners. In specific embodiments, the release liner is a silicone-coated polyester release liner, such as those available from Loparex Inc. (Iowa City, IA). In other specific embodiments, the release liner is a fluoropolymer-coated polyester release liner, such as those available from 3M (St. Paul, MN), including those sold as Scotchpak™ 9744.

Methods of Manufacture

The transdermal amphetamine compositions and transdermal amphetamine delivery systems described herein can be prepared by methods known in the art, modified as described herein to minimize the reaction of amphetamine with carbon dioxide that leads to the formation of amphetacarbamate/amphetamine carbamate. A typical manufacturing process includes (i) preparing the drug-containing polymer matrix blend by blending (mixing) the polymer matrix components and drug in a suitable solvent, such as a volatile organic solvent or solvent mixture, and blending (mixing) to obtain a homogenous drug-containing polymer matrix solution (sometimes referred to as the "blend"); (ii) casting/coating the blend onto a release liner; (iii) drying the blend (e.g., in an oven) to remove the solvent(s), thereby obtaining dry drug-in-polymer matrix on a release liner. Then, a pre-formed backing layer is applied (typically by lamination) and the resulting product (sometimes referred to as the "laminate") is wound into rolls for storage or further processing into unit dosage forms. To prepare unit dosage forms (e.g., patches) a die is used to cut appropriately sized and shaped pieces, which are packaged into pouches.

To prepare a transdermal amphetamine composition or transdermal amphetamine delivery system as described herein, having low levels of amphetacarbamate/amphetamine carbamate, one or more of the manufacturing steps is conducted under conditions that limit exposure of amphetamine (or a composition comprising amphetamine) to carbon dioxide ($CO_2$), and/or that limit exposure of amphetamine to conditions that promote reaction with $CO_2$. For example, one or more steps may be carried out under an inert gas, such as nitrogen ($N_2$) or argon (Ar), such as preparation of the wet polymer matrix blend, or blending of the wet polymer matrix blend after addition of the amphetamine. Additionally or alternatively, the temperature of the manufacturing room can be controlled. Additionally or alternatively, the time amphetamine spends in a "wet" composition, such as in the wet polymer matrix blend can be limited, in order to limit conditions under which amphetamine reacts with, or readily reacts, with $CO_2$ to form amphetamine carbamate. For example, the blend can be prepared in stages, first blending some or all of the polymer matrix components other than amphetamine, and then adding and blending in the amphetamine. Such a staged process may reduce the time the amphetamine spends in the wet polymer matrix blend. Additionally or alternatively, the drying conditions may be adjusted to adjust (shorten) the drying time (e.g., to shorten the necessary residence time in the oven), such as by adjusting the drying temperature and/or adjusting drying air flow (e.g., air flow in the oven), where increasing the drying temperature and/or increasing drying air flow (e.g., air flow in the oven) generally will shorten the drying time. Shortening the drying time will reduce the time amphetamine spends in a "wet" polymer matrix solution. Additionally or alternatively, other process parameters may be adjusted to limit the time amphetamine spends in a "wet" polymer matrix blend, such as by adjusting the speed at which the wet polymer matrix material travels along the processing line, wherein increasing the speed at which the wet polymer matrix material travels along the processing line (e.g., increasing the "web" speed), such as by increasing the speed/decreasing the time from the coating site/step to the drying site/step (e.g., oven) and/or increasing the speed/decreasing the time travelling through the drying region (e.g., oven), generally will reduce the time amphetamine spends in a "wet" polymer matrix blend. Such changes will reduce the time amphetamine spends a "wet" polymer matrix blend. Additionally or alternatively, other process parameters may be adjusted to reduce the risk of exposure to $CO_2$. or that limit exposure of amphetamine to conditions that promote reaction with $CO_2$. Those skilled in the art will understand that the selection of process parameters to reduce amphetamine reaction with $CO_2$ may be balanced against other objectives, such as limiting drug loss during the manufacturing process, as discussed below.

Because amphetamine free base is a volatile liquid drug, some amount of drug typically is lost during the manufacturing process, such that the amphetamine content of the wet polymer matrix blend is greater than that of the dry drug-containing polymer matrix. This can be accounted for by increasing the amount of amphetamine used to prepare the wet polymer matrix blend in order to obtain the target amphetamine content in the dry drug-containing polymer matrix (sometimes referred to as a "manufacturing overage"). Along the same lines, embodiments disclosed herein using more intense drying conditions (e.g., increasing the drying temperature and/or air flow) can lead to increased volatilization and loss of drug. This can be accounted for by (further) increasing the amount of amphetamine used to prepare the wet polymer matrix blend in order to obtain the target amphetamine content in the dry drug-containing polymer matrix after drying under the more intense conditions (e.g., increasing the manufacturing overage).

The coat weight of the drug-containing polymer matrix is selected and controlled during the coating step of the manufacturing process. As discussed above, in accordance with any embodiments described herein, the coat weight of the drug-containing polymer matrix can be from about 3 $mg/cm^2$ to about 10 $mg/cm^2$, or to about 15 $mg/cm^2$, based on the active surface area. Exemplary coat weights include about 3 $mg/cm^2$, about 4 $mg/cm^2$, about 5 $mg/cm^2$, about 5.5 $mg/cm^2$, about 6 $mg/cm^2$, about 6.5 $mg/cm^2$, about 7 $mg/cm^2$, about 7.5 $mg/cm^2$, about 8 $mg/cm^2$, about 8.5 $mg/cm^2$, about 9 $mg/cm^2$, about 9.5 $mg/cm^2$, about 10 $mg/cm^2$, about 12.5 $mg/cm^2$, about 15 $mg/cm^2$, or greater, including 3 $mg/cm^2$, 4 $mg/cm^2$, 5 $mg/cm^2$, 5.5 $mg/cm^2$, 6 $mg/cm^2$, 6.5 $mg/cm^2$, 7 $mg/cm^2$, 7.5 $mg/cm^2$, 8 $mg/cm^2$, 8.5 $mg/cm^2$, 9 $mg/cm^2$, 9.5 $mg/cm^2$, 10 $mg/cm^2$, 12.5 $mg/cm^2$, 15 $mg/cm^2$, or greater, all based on the dry coat weight. In specific embodiments the coat weight of the polymer matrix is about 6.0 to about 8.0 $mg/cm^2$, including about 7.0 $mg/cm^2$, based on the active surface area of the of the polymer matrix.

As set forth above, the amphetamine content per unit area depends on the concentration of amphetamine in the drug-containing polymer matrix and the coat weight of the polymer matrix. In specific embodiments, the actual or target amphetamine content is from about 0.50 $mg/cm^2$ to about 3.0 $mg/cm^2$ of the active surface area of the drug-containing polymer matrix, such as about 1.0 $mg/cm^2$ of the active surface area, including about 1.05 $mg/cm^2$ of the active surface area. Other exemplary actual or target amounts include about 0.75 $mg/cm^2$, about 0.8 $mg/cm^2$, about 0.9 $mg/cm^2$, about 1.0 $mg/cm^2$, about 1.05 $mg/cm^2$, about 1.1 $mg/cm^2$, about 1.2 $mg/cm^2$, about 1.25 $mg/cm^2$, about 1.5 $mg/cm^2$, about 2.0 $mg/cm^2$, about 2.5 $mg/cm^2$, and about 3.0 mg/cm$^2$, including 0.75 mg/cm$^2$, 0.8 mg/cm$^2$, 0.9 mg/cm$^2$, 1.0 mg/cm$^2$, 1.05 mg/cm$^2$, 1.1 mg/cm$^2$, 1.2 mg/cm$^2$, and 1.25 mg/cm$^2$, 1.5 mg/cm$^2$, 2.0 mg/cm$^2$, 2.5 mg/cm$^2$, and 3.0 mg/cm$^2$.

The size of a unit dosage form of a transdermal amphetamine composition or amphetamine transdermal delivery system as described herein (e.g., an individual patch) typically will be in the range of from about 2 cm$^2$ to about 60 cm$^2$, including from about 5 cm$^2$ to about 30 cm$^2$, including about 4.75 cm$^2$, 5 cm$^2$, 10 cm$^2$, 15 cm$^2$, 20 cm$^2$, 25 cm$^2$, and 30 cm$^2$. In typical product lines, the same drug-containing polymer matrix (having the same amphetamine content and coat weight) may be used to make all doses ("strengths"), with the size of the individual systems being selected to provide the target amphetamine content per unit dosage form. For example, in specific embodiments, the final product may include an amount of amphetamine of about 1.05 mg/cm$^2$, such that, for example, a 5 cm$^2$ system includes about 5.25 mg amphetamine, and systems having a size of 10 cm$^2$, 15 cm$^2$, 20 cm$^2$, 25 cm$^2$, and 30 cm$^2$ have proportionate amounts of amphetamine.

Methods of Detecting Amphetacarbamate

As noted above, the existence or identity of amphetamine carbamate or amphetacarbamate per se were not known. Rather, amphetamine carbamate was identified and characterized by analyzing crystals isolated from drug-containing polymer matrices of transdermal amphetamine compositions, and amphetacarbamate was identified the work done to identify and characterize amphetamine carbamate. In addition to the inventions described herein pertaining to transdermal amphetamine compositions and amphetamine transdermal delivery systems, methods for detecting and quantifying amphetamine carbamate had to be developed. This proved to be a particularly difficult undertaking because, for example, in solution, the amphetacarbamate moiety of amphetamine carbamate is labile and readily converts to amphetamine. Thus, for example, typical HPLC assays could not be used.

Figure 2A:
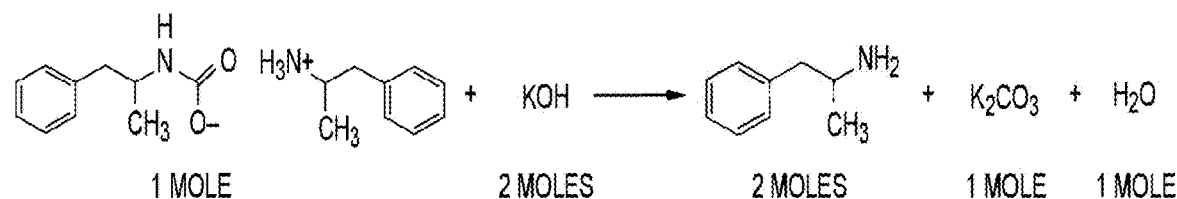
FIG. 2A-2B illustrate reaction schemes for the reaction of amphetamine carbamate with potassium hydroxide (KOH) to yield amphetamine, potassium carbonate, and water.
Figure 2B:
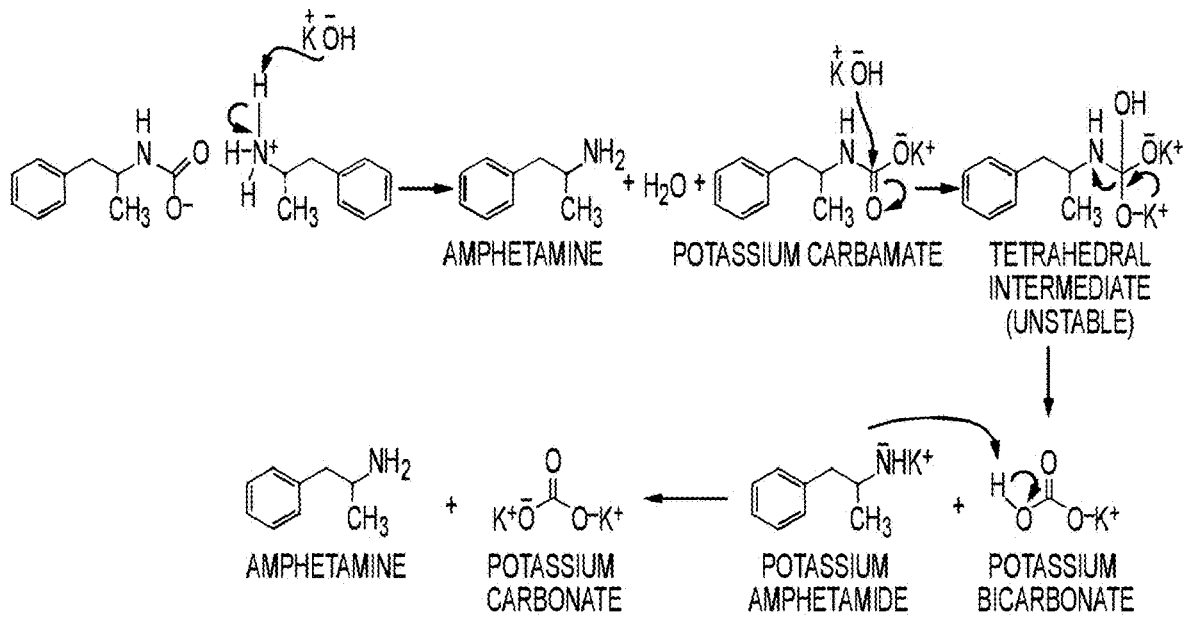
Figure 3:
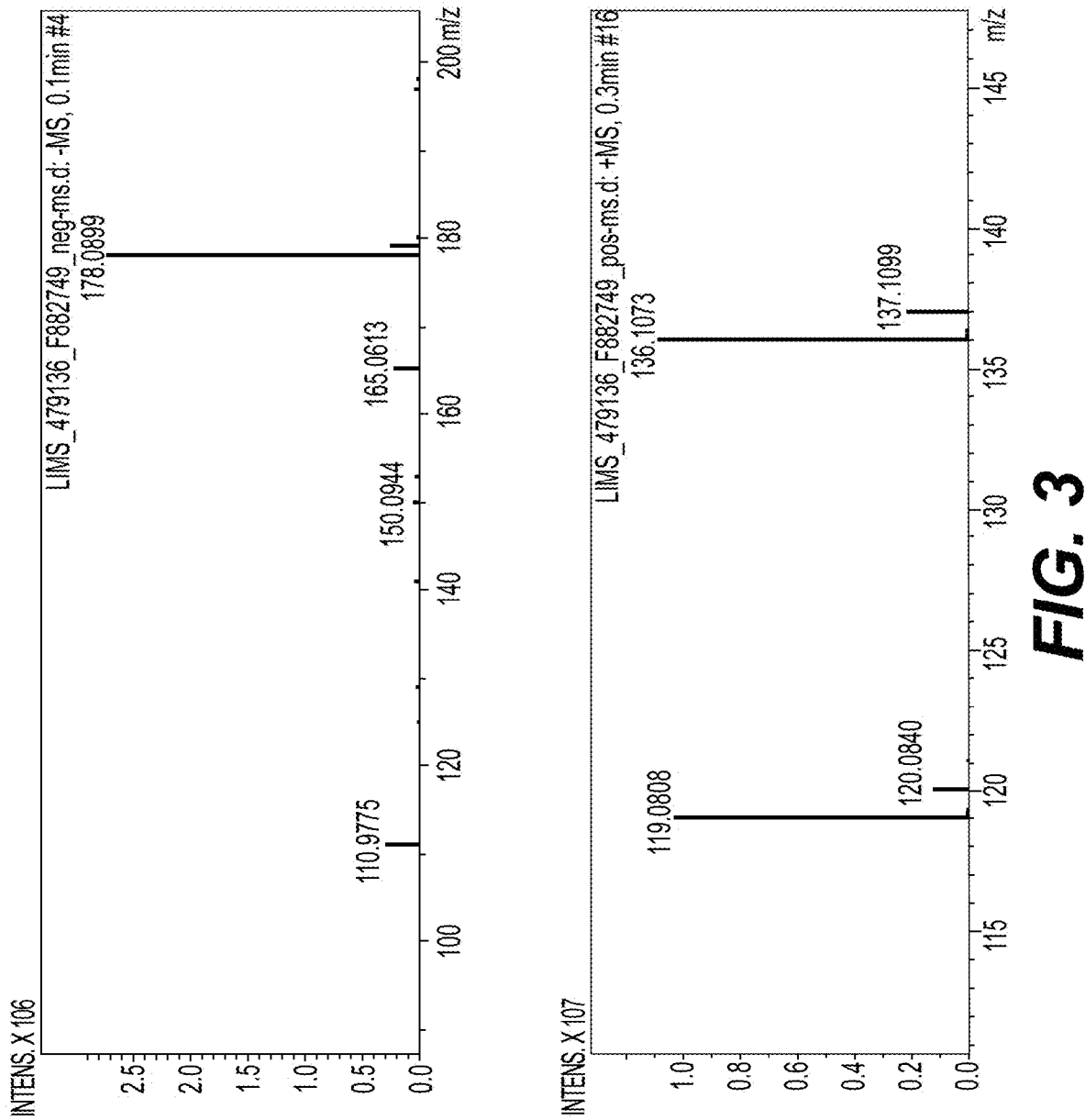
FIG. 3 sets forth results of high resolution mass spectrometry (MS) analysis of amphetamine carbamate performed in negative ion mode (top panel) and positive ion mode (bottom panel).
Figure 4:
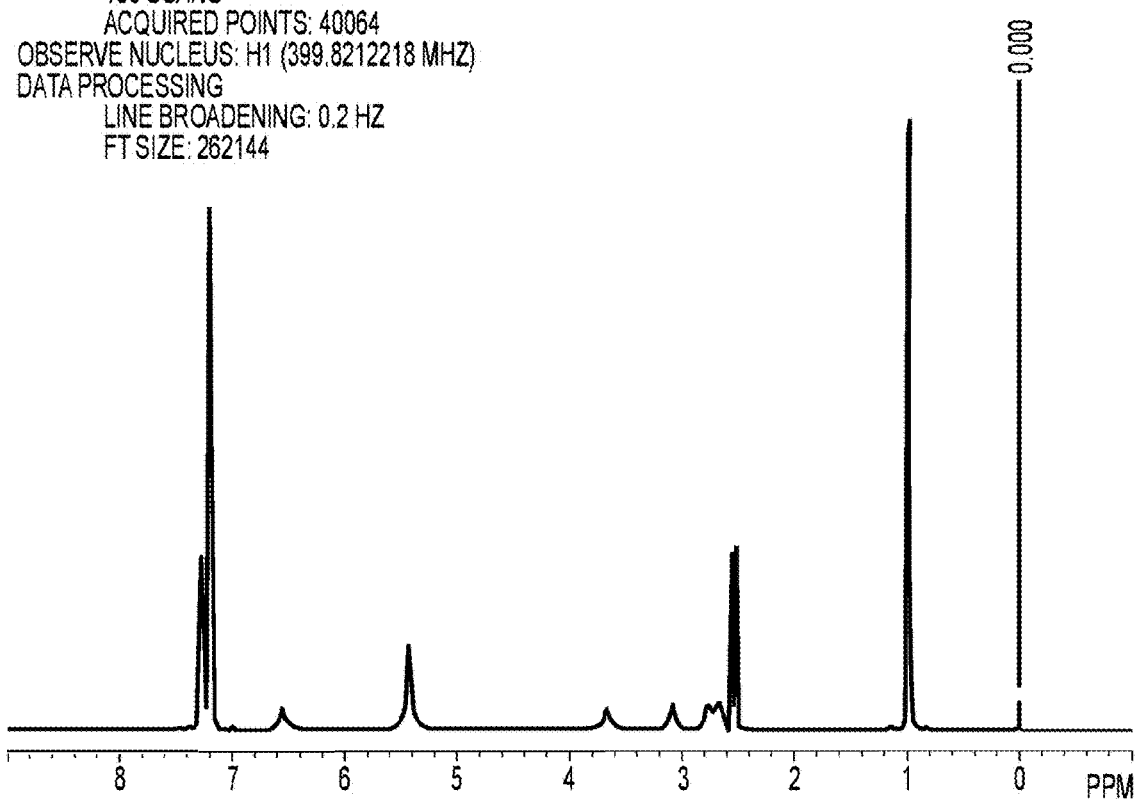
FIG. 4 sets forth results of a $^1$H NMR spectral analysis of amphetamine carbamate.
Figure 5:
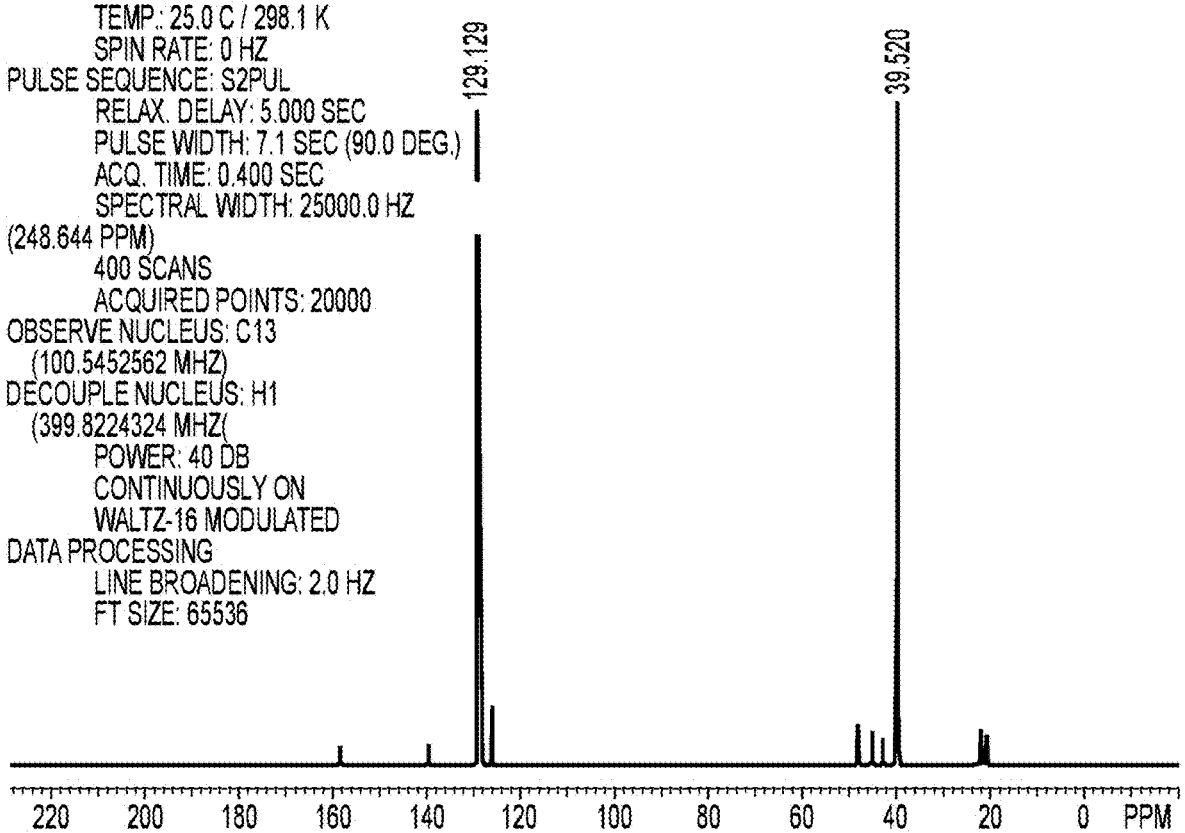
FIG. 5 sets forth results of a $^{13}$C NMR spectral analysis of amphetamine carbamate.
Figure 6:
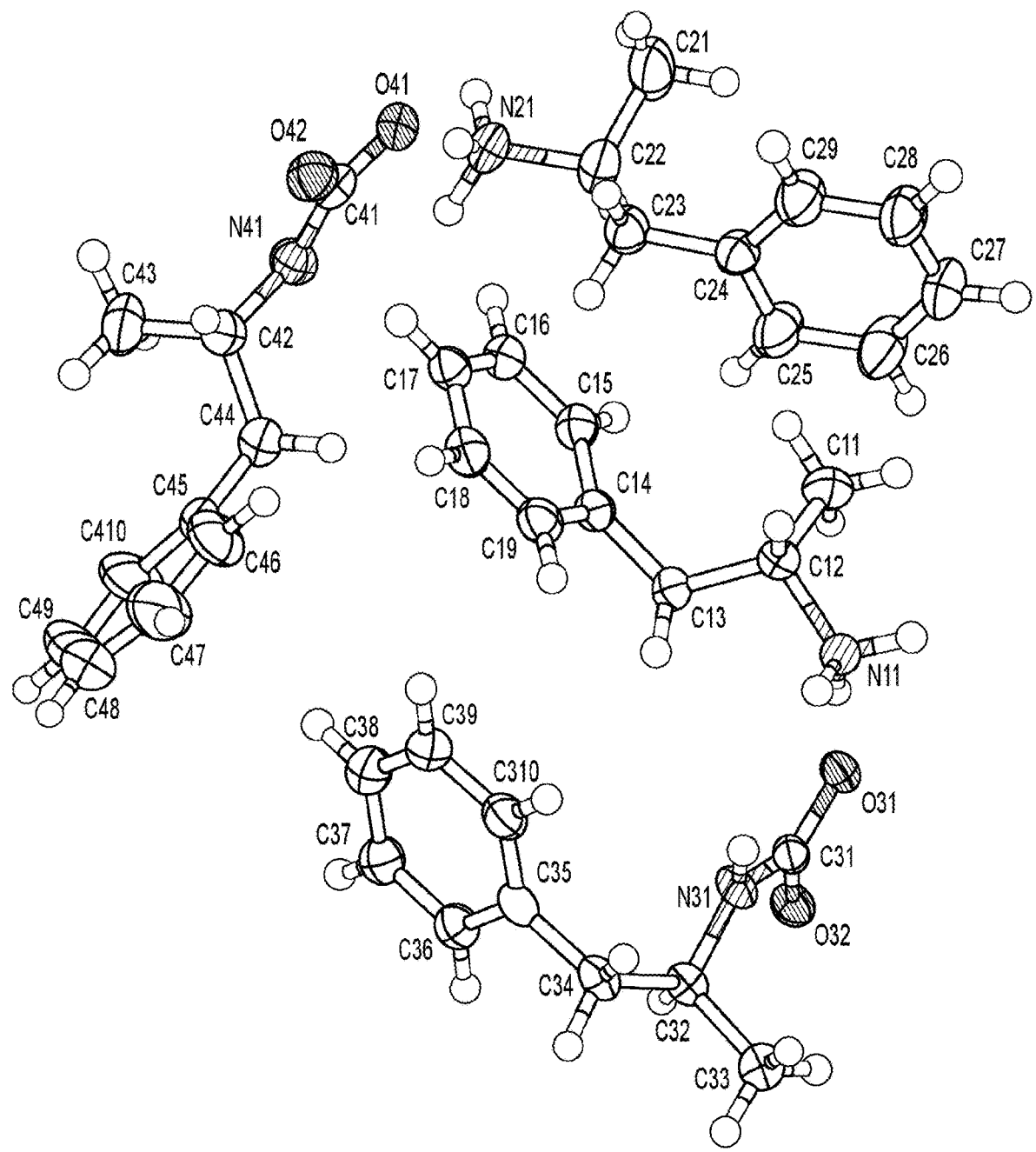
FIG. 6 illustrates the crystal structure of amphetamine carbamate based on single crystal powder x-ray diffraction analysis.
Figure 7:
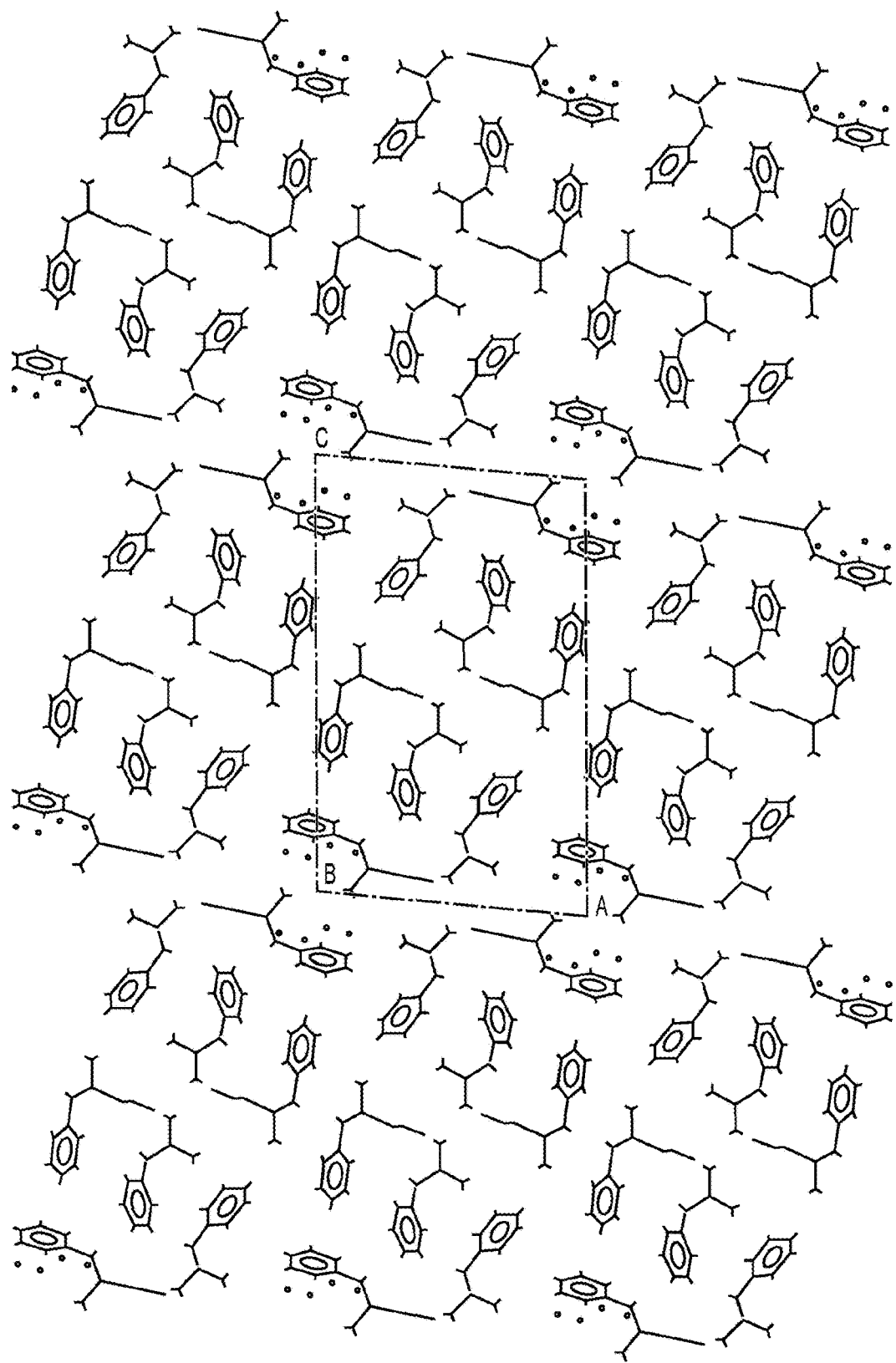
FIG. 7 provides a packing diagram for crystalline amphetamine carbamate viewed along the crystallographic b axis.
Figure 8:
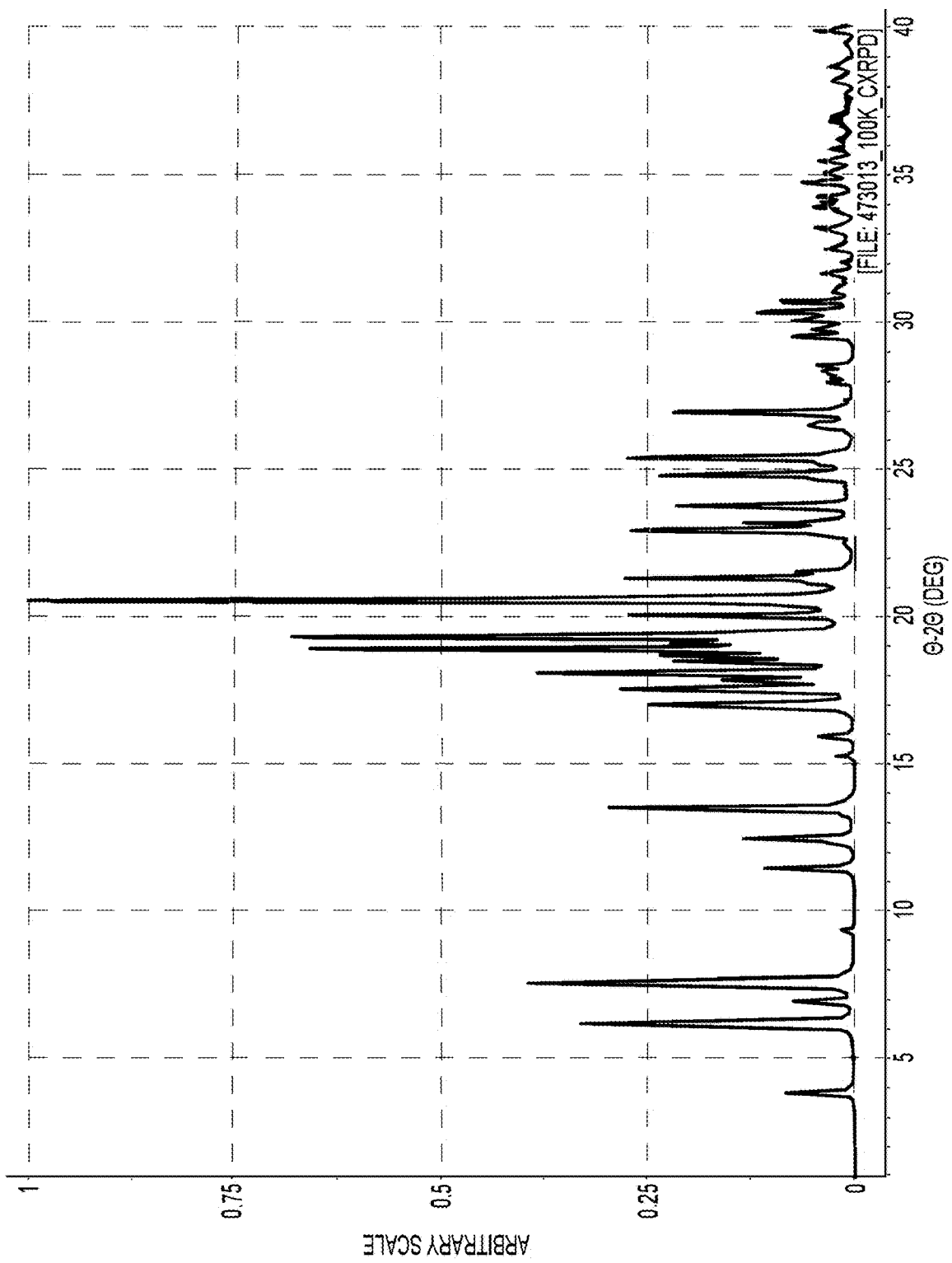
FIG. 8 sets forth a calculated x-ray powder diffraction pattern for crystalline amphetamine carbamate viewed along the crystallographic b axis.

As described in co-pending U.S. provisional application 63/134,852, filed Jan. 7, 2021, by Applicant Noven Pharmaceuticals, Inc., entitled "AMPHETAMINE CARBAMATE COMPOUNDS AND METHODS," an ion chromatography (IC) assay for amphetacarbamate was developed and validated. The assays are based on detection of carbonate ion generated from in situ reaction of amphetamine carbamate with a reagent that reacts in situ with the amphetacarbamate to produce carbonate ion, such as a base (e.g., potassium hydroxide or sodium hydroxide or lithium hydroxide). The reagent may be provided in situ by spiking the chromatography eluent with the reagent. While not wanting to be bound by theory, the current understanding of the reaction at issue is illustrated in FIG. 2A and FIG. 2B with reference to specific embodiments using KOH as the reagent. Again while not wanting to be bound by theory, and as depicted in FIG. 2B, it is believed that a first molecule of, e.g., KOH, acts as base and reacts with the acidic proton of the amphetammonium moiety of amphetamine carbamate to generate free amphetamine base and potassium carbamate. Then, a second molecule of, e.g., KOH, acts as a nucleophile and reacts with the electrophilic carbon atom of potassium carbamate to yield an unstable tetrahedral intermediate. The unstable tetrahedral intermediate readily decomposes into potassium bicarbonate and potassium amphetamide, which is a strong base. Then, potassium amphetamide acts as a base and reacts with the acidic hydrogen of potassium bicarbonate to generate a second molecule of amphetamine and potassium carbonate, which is the moiety detected and quantitated by IC. Therefore in the overall reaction, one mole of amphetamine carbamate reacts with two moles of, e.g., KOH, to yield two moles of amphetamine, one mole of potassium carbonate, and one mole of water, as set forth in FIG. 2A. The assay preferably is conducted under inert conditions, including conditions that minimize exposure of the test composition to the environment or other reactive species, to avoid or limit the production or introduction of additional amphetamine carbamate, amphetacarbamate and/or carbonate (other than the intended in situ production from reaction of amphetacarbamate).

Sample Preparation for IC Assay

In order to determine whether amphetamine carbamate/amphetacarbamate is present in transdermal amphetamine compositions or amphetamine transdermal delivery systems, or to quantitate the amount present therein, in accordance with the methods described herein, the compositions/systems are first prepared for ion chromatography analysis, preferably under conditions that prevent or minimize risk of (further) production of amphetamine carbamate. For example, a sample can be prepared from an amphetamine-containing polymer matrix (or transdermal amphetamine composition or amphetamine transdermal delivery system) by a process comprising (i) immersing a drug-containing polymer matrix comprising amphetamine, amphetacarbamate, and polymer components in an organic solvent, to obtain an extraction mixture; (ii) subjecting the extraction mixture to sonication; (iii) adding a sample diluent (e.g., consisting of a mixture of the organic solvent and reagent grade water) to the extraction mixture to induce precipitation of the polymer components while maintaining the amphetamine and amphetacarbamate in solution, to obtain a composition comprising a precipitate; (iv) filtering the composition comprising a precipitate to remove the precipitate, thereby obtaining a composition comprising amphetamine and amphetacarbamate in solution. The resulting composition, or a sample or aliquot thereof, can be used as the test sample in an IC assay as discussed below.

In some embodiments, one or more of the sample preparation steps (e.g. one or more of steps (i)-(iv)) may be conducted under inert conditions, such as conditions that minimize exposure of the composition to, e.g., carbon dioxide, such as under an inert atmosphere (e.g., under nitrogen or argon gas), to avoid or limit the production or introduction of additional amphetamine carbamate, amphetacarbamate and/or carbonate, such as by avoiding or limiting reaction of amphetamine with carbon dioxide, which may form additional amphetamine carbamate/amphetacarbamate. (Such precautions also may be taken during any one or more or all steps of the IC assay.) Additionally or alternatively, the solvents used in one or more of the sample preparation steps may be solvent that has been purged with an inert gas. For example, the organic solvent may be an inert gas-purged organic solvent, such as inert gas-purged methanol, such as helium-purged methanol. Additionally or alternatively, the sample diluent may be an inert gas-purged organic solvent, such as inert gas-purged methanol, such as helium-purged methanol, and reagent grade water. In specific embodiments, the sample diluent consists of a mixture of the same organic solvent used for step (i) and reagent grade water. Thus, for example, the organic solvent may be an inert gas-purged organic solvent, such as inert gas-purged methanol, such as helium-purged methanol, and the sample diluent consists of a mixture of the same organic solvent and reagent grade water.

Thus, to analyze a transdermal amphetamine composition or amphetamine transdermal delivery system for amphetamine carbamate/amphetacarbamate content, one or more of the following steps may be conducted in an inert atmosphere, such as under nitrogen or argon gas, to prepare a sample for IC analysis:

Remove any release liner present.

Optionally, apply the drug-containing polymer matrix (including the backing layer, if present) to a piece of filter paper previously sized to be slightly larger than the surface area of the drug-containing polymer matrix, and optionally hold the unit in place with, e.g., an appropriate number of paper clips.

Immerse the drug-containing polymer matrix (including the backing layer, if present) in an organic solvent in a closed glass jar, to obtain an extraction mixture.

Subject the extraction mixture to, e.g., sonication, to thoroughly expose/subject the polymer matrix components to the organic solvent.

Add a sample diluent to the extraction mixture to induce precipitation of the polymer components while maintaining the amphetamine and amphetacarbamate in the organic solvent, to obtain a composition comprising a precipitate.

Filter the composition comprising a precipitate (or an aliquot thereof) to remove the precipitate, thereby obtaining a composition comprising amphetamine and amphetacarbamate in the organic solvent.

For preparation of a sample blank for such a sample for use in an IC assay as described below, the same steps would be followed without using the drug-containing polymer matrix. For example, if used, the same sized filter paper would be immersed in the same organic solvent, subject to the same sonication, addition of the same sample diluent, etc.

IC Assays

An IC assay may be conducted as follows to determine whether amphetamine carbamate/amphetacarbamate is present in a transdermal amphetamine composition or amphetamine transdermal delivery system, or to quantitate the amount present therein.

The IC eluent is inert-gas purged deionized water spiked with the reagent that reacts in situ with the amphetacarbamate to produce carbonate ion, such as a base, such as a base that provides a basic hydroxide ion, such as an aqueous alkali or earth alkali hydroxide salt, such as potassium hydroxide (KOH), sodium hydroxide (NaOH) or lithium hydroxide (LiOH). When the reagent is KOH, NaOH, or LiOH, the stoichiometric relationship between amphetacarbamate (or amphetamine carbonate) and carbonate ion for quantifying the amphetacarbamate (or, optionally, amphetamine carbonate) originally present in the composition from the quantified amount of carbonate ion in the reaction products is 1:1, as illustrated in FIG. 2A. The concentration of the reagent in the eluent may be any suitable concentration effective to react with any and all amphetacarbamate present in the test sample to yield carbonate ion, under the conditions of the specific IC assay at issue (including, e.g., column size, flow rate, etc.). Example reagent concentrations include from about 1 mM to about 100 mM. including about 1, 5, 10, 15, 20, 25, 30, 35, 40, 45, 50, 75, or 100 mM, such as about 5, 10, 15, 20 or 25 mM. In certain embodiments, the eluent is inert-gas purged deionized water spiked with 10 mM KOH. The inert gas used for the inert-gas purged deionized water is not particularly limited, and may be, for example, helium.

As explained above, the IC assays disclosed herein are based on detection of carbonate ion (which has a molecular weight of 60.01 g/mol), generated from in situ reaction of amphetamine carbamate. Thus, any IC columns suitable for separating carbonate ion may be used, including an analytical column packed with a suitable resin and a guard column packed with a suitable resin. Suitable resins include those that are capable of separating inorganic anions in high-purity aqueous matrices, such as resins comprising alkanol quaternary ammonium cations as ion exchange groups. Specific examples of such resins include IonPac® AG17-C (analytical column) and IonPac® AG17-C (guard column). For example, for the stationary phase, a 250×4 mm analytical column (such as IonPac® AS17-C) and a 50×4 mm guard column (such as IonPac® AG17-C) may be used, both packed with alkanol quaternary ammonium resin having a particle size of 10.5 µm. The column(s) may be maintained at any suitable temperature, such as a constant temperature of 30° C.±2° C. Thu, in use, an IC column may include the resin, an aqueous solution comprising the reagent, and two or more of amphetacarbamate, amphetamine, and carbonate ion, such as a column comprising (i) alkanol quaternary ammonium resin, (ii) KOH, NaOH or LiOH, and (iii) two or more of amphetacarbamate, amphetamine and carbonate ion.

Any ion chromatogram suitable for detecting and quantifying carbonate by the assays disclosed herein may be used. Thus, for example, the ion chromatograph may include appropriate configurations suitable for the disclosed assays. Specific examples of suitable ion chromatographs include Dionex™ ICS-5000+ and ICS-6000 HPIC systems. In specific embodiments, the carbonate ion is detected and quantified using a conductivity detector. In further specific embodiments, such as may be implemented to increase sensitivity of carbonate ion detection, a suppressor is connected in series with and prior to the conductivity detector. For example, in some embodiments, the ion chromatograph is equipped with one or more of an autosampler (e.g., a Dionex™ AS-AP Autosampler), an eluent generator (e.g., Dionex™ EGC III KOH, Dionex™ EGC 400 KOH, Dionex™ EGC 500 KOH, Dionex™ EGC III NaOH, Dionex™ EGC III LiOH), a conductivity detector (e.g., Dionex™ ICS-6000 CD Conductivity Detector), and/or a suppressor (e.g., Dionex™ Anion Dynamically Regenerated Suppressor).

Other conditions/parameters of the IC assay and equipment can be selected, adjusted and controlled in accordance with standard practices in the art, keeping in mind a goal of avoiding or limiting conditions that might lead to the production or introduction of additional amphetamine, amphetamine carbamate, amphetacarbamate, and/or carbonate (other than the intended in situ production from reaction of amphetacarbamate), because such produced or introduced amphetamine, amphetamine carbamate, amphetacarbamate and/or carbonate would undermine the accuracy of the detection/quantitation results. For example, the conditions may be selected and controlled to prevent or limit exposure of any amphetamine present to carbon dioxide (because amphetamine may react with carbon dioxide to form additional amphetamine carbamate/amphetacarbamate), and/or may be selected and controlled to prevent or limit exposure to external sources of carbonate.

In some embodiments, the IC assay comprises assaying a series of standard carbonate solutions, each having a different predetermined concentration of carbonate ion, as working standard solution injections for preparation of a calibration curve. The predetermined concentrations of carbonate ion are selected to provide a calibration curve suitable for the test sample, i.e., having an appropriate range of carbonate ion concentrations around (above and below) the target, expected, or predicted carbonate concentration of the test sample. In such embodiments, a regression line of the carbonate ion peak area response (optionally corrected for any carbonate ion peak area response for a standard diluent blank as discussed below) versus carbonate concentration for the working standard solution injections can be plotted as a calibration curve. The amphetacarbamate concentration in the test sample can then be calculated based on the carbonate ion peak area response for the sample injection (optionally corrected for any carbonate ion peak area response for a sample blank as discussed below) with reference to the calibration curve.

Additionally or alternatively, a standard diluent blank and/or a sample blank can be assayed, to assess whether the solvent (diluent) used to prepare the working standard solutions and/or the solvent(s) and any other components used to prepare the sample, or any other aspects of the IC, are contributing to the carbonate ion peak area response. Typically, a standard diluent blank is a preparation of the solvent used to prepare the working standard solutions. Typically, a sample blank is a preparation of the components used to prepare the test sample, other than the test composition itself.

In some embodiments, the IC system suitability and peak symmetry are analyzed to assure that the system and methodology are functioning appropriately. For example, two or more injections of a carbonate working standard solution at the same predetermined concentration can be injected and the relative standard deviation of the carbonate ion peak area response can be assessed. In some embodiments, a relative standard deviation of the carbonate ion peak area response of 5% or less indicates that the system and methodology are functioning appropriately. In some embodiments, the regression coefficient is analyzed to assess suitability of the IC system. In some embodiments, a regression coefficient of not less than 0.990 indicates the system and methodology are functioning appropriately. Additionally or alternatively, in some embodiments, a standard carbonate solution at a predetermined concentration is used as a recovery standard to determine the percent recovery of carbonate ion. The percent recovery may be calculated as shown in the examples. In some embodiments, a percent recovery that does not exceed 15%, or that does not exceed 10%, or that does not exceed 5%, indicates the system and methodology are functioning appropriately. In some embodiments, the tailing factor of carbonate ion peak in the working standard solution injections is determined. In some embodiments, a tailing factor that does not exceed 2.0 indicates the system and methodology are functioning appropriately.

Methods of Use

The compositions and systems described herein are useful in methods for the transdermal delivery of amphetamine, including in methods for treating attention deficit disorder, attention deficit hyperactivity disorder, and/or narcolespy. In such embodiments, a composition or system comprising a therapeutically effective amount of amphetamine as described herein is topically applied to a subject in need thereof.

The compositions described herein achieve a transdermal flux of amphetamine (and/or one or more pharmaceutically acceptable salt(s) thereof) that is sufficient to have a therapeutic effect. As used herein, "flux" (also called "permeation rate") is defined as the absorption of a drug through skin or mucosal tissue, and is described by Fick's first law of diffusion:

$$J = -D(dCm/dx)$$

where J is the flux in $g/cm^2/sec$, D is the diffusion coefficient of the drug through the skin or mucosa in $cm^2/sec$ and dCm/dx is the concentration gradient of the drug across the skin or mucosa.

In some embodiments, the compositions achieve transdermal delivery of amphetamine over a period of time of about 8 to 10 hours, including a period of time of about 9 hours, although the composition may be applied for a shorter or longer period of time. In some embodiments, the compositions achieve transdermal delivery of therapeutically effective amounts of amphetamine over a period of time of about 8 to 10 hours, including a period of time of about 9 hours, although the composition may be applied on the application site for a shorter or longer period of time.

The following specific examples are included as illustrative of the methods, compositions and systems described herein. These example are in no way intended to limit the scope of the invention. Other aspects of the invention will be apparent to those skilled in the art to which the invention pertains.

EXAMPLES

Figure 11:
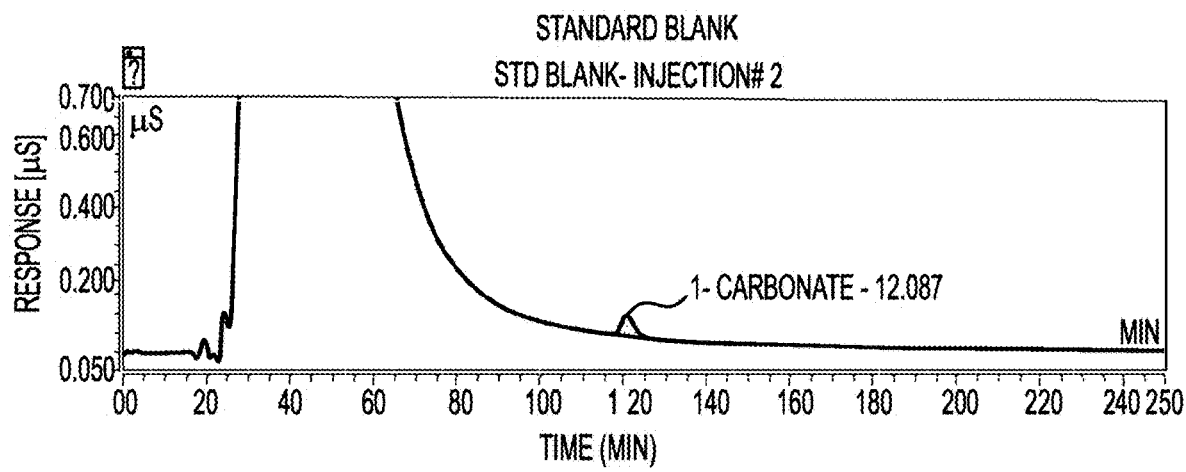
FIG. 11 sets forth a typical chromatogram for a standard diluent blank ("Standard Blank"), a carbonate working standard solution ("Standard D"), and a sample prepared from an amphetamine transdermal drug delivery system.
Figure 11:
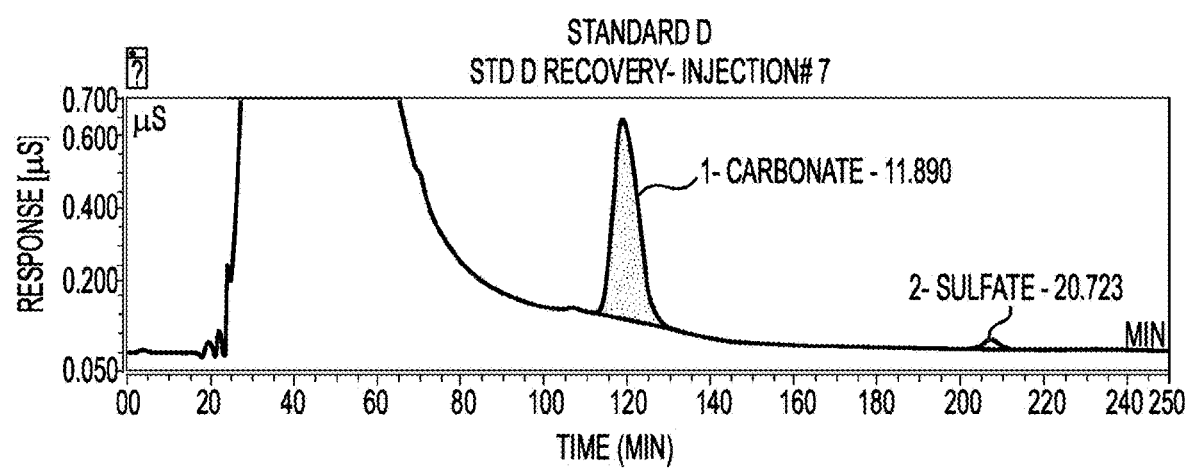
Figure 11:
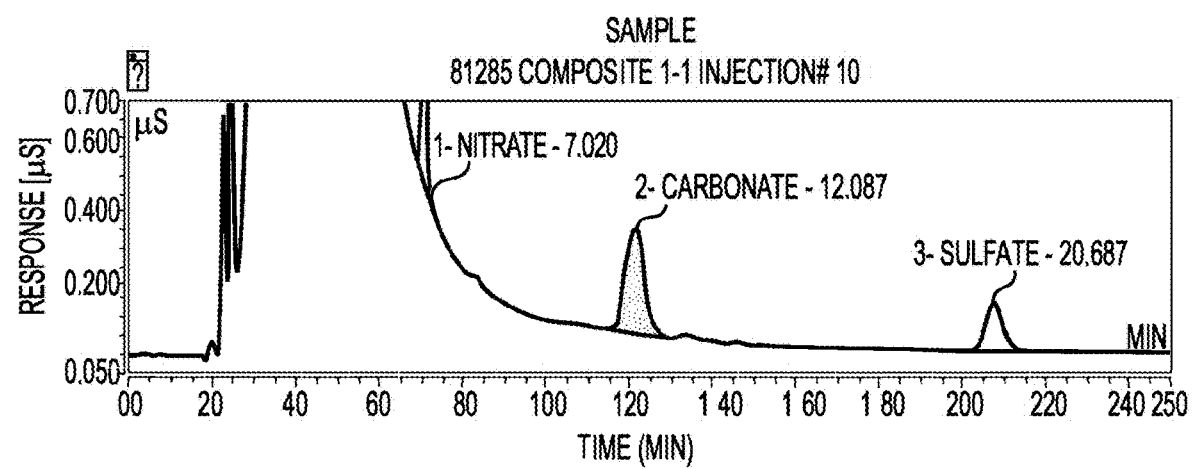

Example 1—Detection of Amphetacarbamate in a Polymer Matrix by Ion Chromatography An example of a specific IC assay for quantitation of amphetacarbamate in a sample prepared from an amphetamine drug-containing polymer matrix is provided. Typical chromatograms for a standard diluent blank, a standard working solution, and a sample for such an assay is set forth in FIG. 11.

Sample and Sample Blank Preparation

Sample preparation is conducted under an inert gas, such as nitrogen or argon gas. A drug-containing polymer matrix is subject to dissolution/extraction in a closed glass jar using helium-purged methanol as an extraction solvent and subject to sonication. Then, helium-purged methanol/water (5%/95%) is added as a sample diluent to precipitate the adhesive components. In the calculations below, the total volume of the extraction solvent and sample diluent used (combined) is referred to as the Sample Volume. The sample (or an aliquot thereof) is filtered using a polytetrafluoroethylene (PTFE) filter and transferred to an IC tube for use in the IC assay. A sample blank is prepared by the same process, without using a drug-containing polymer matrix.

Standard and Standard Diluent Blank Preparation

Carbonate stock standard solutions and carbonate working standard solutions are prepared for purposes of creating a calibration curve.

To produce a Carbonate Stock Standard Solution, 27 mg of sodium carbonate is transferred into a 250 mL volumetric flask. 100 mL of Standard Diluent (helium-purged Methanol/Water, 30%:70%, v/v) is added to the flask and sonicated for five minutes to dissolve. The solution is allowed to cool inside a glove box under nitrogen and diluted to volume (250 mL) with Standard Diluent.

The carbonate ion concentration in the Carbonate Stock Standard Solution is calculated as follows:

$$\text{Carbonate Ion } (\mu g/mL) = \frac{(W)(\text{Potency})(0.56619)(1000)}{(250)}$$

W=weight of Sodium Carbonate Standard (mg) (27 mg in this example);

Potency=potency (purity) of sodium carbonate used;

0.56619=ratio of the molecular weights of carbonate ion to sodium carbonate;

1000=unit conversion of mg to μg; and

250=volume in mL.

Carbonate working standard solutions are prepared at appropriate concentrations to prepare a calibration curve for the test sample. For this example, working standard solutions are prepared as follows:

Working Standard A ("STD A") (Approximately 0.6 μg/ml of Carbonate Ion): Pipette 2.0 ml of Stock Standard Solution into a 200 ml volumetric flask. Dilute to volume with Standard Diluent and mix well.

Working Standard B ("STD B") (Approximately 1.5 μg/ml of Carbonate Ion): Pipette 5.0 ml of Stock Standard Solution into a 200 ml volumetric flask. Dilute to volume with Standard Diluent and mix well.

Working Standard C ("STD C") (Approximately 3 μg/ml of Carbonate Ion): Pipette 5.0 ml of Stock Standard Solution into a 100 ml volumetric flask. Dilute to volume with Standard Diluent and mix well.

Working Standard D ("STD D") (Approximately 5 μg/ml of Carbonate Ion): Pipette 4.0 ml of Stock Standard Solution into a 50 ml volumetric flask. Dilute to volume with Standard Diluent and mix well.

Standard D Recovery ("STD D Recovery") (Approximately 5 μg/ml of Carbonate Ion): Pipette 4.0 ml of Stock Standard Solution into a 50 ml volumetric flask. Dilute to volume with Standard Diluent and mix well.

A standard diluent blank is prepared by purging Methanol/Water (30%: 70%, v/v) with helium.

Ion Chromatography

The IC can be carried out using standard equipment, but adjustments are required to separate and quantify carbonate ions, as illustrated below.

Assay

The IC is set up with the following conditions.

For the stationary phase, a 250×4 mm analytical column (such as IonPac® AS17-C) and a 50×4 mm guard column (such as IonPac® AG17-C) is used, both packed with resin comprising alkanol quaternary ammonium cations as ion exchange groups with particle size of 10.5 μm. The columns are maintained at a constant temperature of 30° C.±2° C.

The eluent is helium-purged deionized water. For the in situ reaction, 10 mM potassium hydroxide is delivered into the eluent by an eluent generator. The reagent-spiked eluent (helium-purged deionized water spiked with 10 mM KOH) is pumped through the system at a constant flow rate of 1.0 mL/minute.

A conductivity detector is used for detection of carbonate ion in the eluent, with a sampling rate of 5 Hz. The detector cell heater temperature is set to 35° C. Sensitivity of carbonate ion detection is improved with the aid of a suppressor connected in series but prior to the detector (such as a Dionex ADRS 600 suppressor).

An injection volume of 100 μL is used with a run time of 25 minutes. The typical retention time for carbonate ion is 9-13 minutes. A typical relative retention time for nitrate ion that may be present is about 0.59 times that of carbonate ion, while a typical relative retention time for sulfate ion that may be present is about 1.72 times that of carbonate ion.

An exemplary chromatographic sequence is shown in Table 2, starting with the injections used to prepare the calibration curve. It should be understood that multiple blanks, standards, and/or sample injections can be used, with the average of the results of each type used in the calculations below. However, if only one blank injection of a given type yields a peak area for carbonate ion, use that peak area rather than an average.

TABLE 2

Exemplary Chromatographic Sequence(s)-
Amphetamine Transdermal System

| Injection Number | Description |
|---|---|
| Standard Calibration Curve: | |
| 1 | Standard Diluent Blank |
| 2 | STD A |
| 3 | STD B |
| 4 | STD C |
| 5 | STD D |
| 6 | STD D Recovery |
| Sample Sequence: | |
| 1 | Sample Blank |
| 2 | Sample |
| 3 | Standard Diluent Blank |
| 4 | STD D Recovery |

Calculation of Amphetacarbamate

To determine the amount of amphetacarbamate in the sample, a power regression line is plotted of the carbonate ion peak area response versus concentration for the four working standard solutions injections (STD A, B, C and D). The y-intercept, slope and correlation coefficient of the regression line is calculated according to the following power equation:

$$y = ax^b \quad \text{(Equation 1)}$$

The above equation can be linearized by taking natural logarithm of both sides of the equation to yield equivalent equation (2) below:

$$\ln(y) = \ln(a) + b \ln(x) \quad \text{(Equation 2)}$$

where:

y=peak area response of carbonate ion from the working standard solution injection (e.g. STD A) minus peak area response of carbonate ion from the standard diluent blank injection. If no carbonate ion peak is detected in the standard diluent blank injection, use the peak area response from the working standard solution injection in the calculation;

x=concentration of carbonate ion in the working standard solution (g/mL);

b=slope from regression line of standards; and ln(a)=y-intercept.

Equation 2 can be rewritten as:

$$\ln(x) = \frac{\ln(y) - \ln(a)}{b}. \quad \text{(Equation 3)}$$

The concentration of carbonate (x), is expressed in exponential form of Equation 3 as shown below:

$$X = e^{\frac{\ln(y) - \ln(a)}{b}}.$$

The amount of amphetacarbamate present in the sample is calculated based on the amount of carbonate ion detected according to the top equation below (Equation 4A):

Equations 4A and 4B $$\text{mg Amphetacarbamate} = e^{\frac{\ln(A_{SPL})-\ln(a)}{b}} \times \frac{V_{SAMP}}{1000} \times 2.96967$$

$$\% \text{ Amphetacarbamate} = \frac{\text{mg Amphetacarbamate}}{LC} \times 100$$

where:

$A_{SPL}$=peak area response of carbonate ion from the sample injection minus the peak area response of carbonate ion from the sample blank injection. If no carbonate ion peak is detected in the sample blank injection, then the peak area response from the sample solution injection is used in the calculation;

ln(a)=y-intercept;

b=slope;

$V_{SAMP}$=Sample Volume (mL) (see Sample Preparation step above);

1000=unit conversion from g to mg; and 2.96967=ratio of the molecular weights of amphetacarbamate to carbonate ion (178.21/60.01).

The amount of amphetacarbamate present in the sample relative to the target amount of amphetamine present in the drug-containing polymer matrix used to prepare the sample (e.g., the "Label Claim" amount, or "LC") is calculated based on the amount of carbonate ion detected according to the top and bottom equations above (Equations 4A and 4B), where LC is the Label Claim amount for amphetamine (mg) in the drug-containing polymer matrix used, which is the target amount of amphetamine (mg) in the drug-containing polymer matrix used to prepare the sample (e.g., the patch or portion thereof used) (e.g., the amount that would be indicated as present on final product labeling, such as the FDA-approved product label), and 100 is the unit conversion to percent. Similar equations could be used to calculate the amount of amphetacarbamate present in the sample relative to a different basis, such as relative to the actual amount of amphetamine present in a drug-containing polymer matrix obtained from the same lot, or same region of the polymer matrix (as determined by HPLC, for example), or relative to the target amphetamine content of the dry polymer matrix (% wt/wt). Parallel calculations may be used to determine the amount of amphetamine carbamate present in the original composition by using the molecular weight of amphetamine carbamate instead of the molecular weight of amphetacarbamate in Equation 4B.

System Suitability

System suitability and peak symmetry can be evaluated to assure that the measuring system and the methodology are functioning appropriately. For example, successive injections of the same working standard solution (having the same predetermined carbonate ion concentration) can be made, and the relative standard deviation (RSD) of the peak area response of carbonate ion can be calculated and corrected for blank (standard diluent blank) as described above. Typically, it is desired that the % RSD does not exceed 5%. Typically, it is desired that the regression coefficient (r) is not less than 0.990. Additionally or alternatively, the % recovery of a carbonate working standard can be calculated as a check on the working standard, as illustrated by the Standard D Recovery solution in Table 2. In this example, the goal for the target % recovery for the Standard D Recovery solution injected following the four working standard solutions injections (STD A, B, C and D), is not to exceed 10%, while the goal for the target % recovery for the Standard D Recovery solution injected following the sample injection is to not exceed 15%.

$$\% \text{ Recovery} = \left|\frac{Conc._{STD} - Calc\ Conc._{STD}}{Conc._{STD}}\right| \times 100$$

where:

Conc.$_{STD}$=Theoretical concentration of Standard D Recovery solution (g/mL); and Calc Conc.$_{STD}$=Concentration of Standard D Recovery solution calculated from power regression curve.

$$Calc\ Conc_{STD} = e^{\frac{\ln(A_{STD})-\ln(a)}{b}}$$

where:

$A_{STD}$=Peak area response of carbonate ion from the Standard D Recovery injection minus peak area response of carbonate ion from standard diluent blank injection. If no carbonate ion peak is detected in the standard diluent blank injection, the peak area response from the Standard D Recovery injection is used in the calculation;

ln(a)=y-intercept; and b=slope.

The Tailing Factor (T) of the carbonate ion peak from standard solution injections can be assessed. A typical goal is that it does not exceed 2.0.

Example 2—Detection of Amphetacarbamate in Amphetamine API

Figure 12:
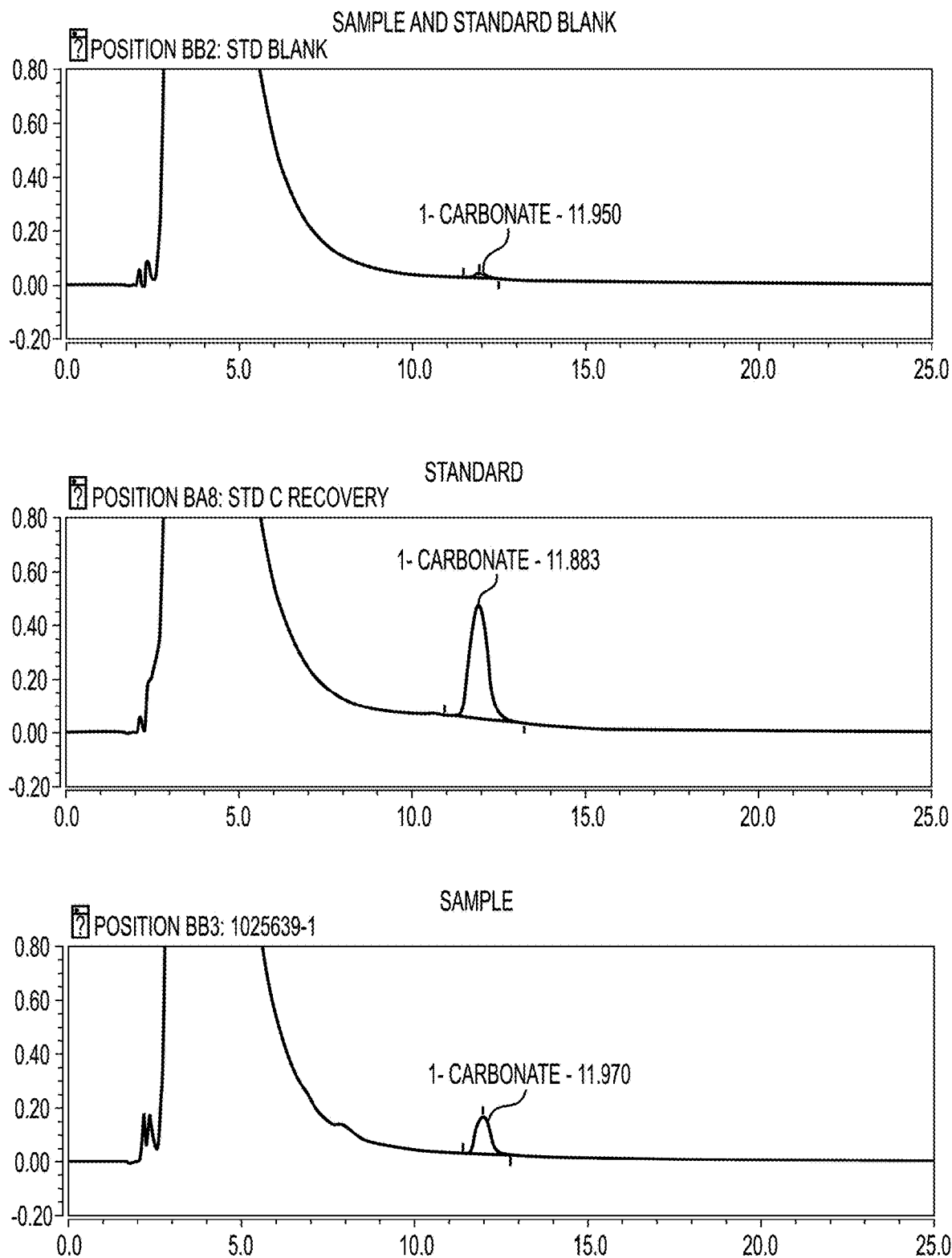
FIG. 12 sets forth a typical chromatogram for a sample/standard diluent blank ("Sample and Standard Blank"), a carbonate working standard solution ("Standard"), and a sample prepared from d-amphetamine active pharmaceutical ingredient ("API").

An IC assay as described herein can be used to detect or quantitate amphetacarbamate in amphetamine API. The IC assay is similar to that described for Example 1, except where noted below. A typical chromatogram for a sample and standard diluent blank ("Sample and Standard Blank"), a standard solution ("Standard") and a sample ("Sample") for such an assay is set forth in FIG. 12.

Sample Preparation

Sample preparation is conducted under an inert gas, such as nitrogen or argon gas. 300 mg of amphetamine API, such as d-amphetamine base or l-amphetamine base, is transferred into a 100 mL volumetric flask, diluted to volume (100 mL) with Sample Diluent (helium-purged Methanol/Water, 30%: 70%, v/v), and mixed well. In the calculations below, 100 mL is referred to as the Sample Volume. A portion of the sample solution is transferred into an IC vial for analysis.

Standard and Standard Blank Preparation

Carbonate stock standard solutions and carbonate working standard solutions are prepared for purposes of creating a calibration curve, as generally described in Example 1.

For the present example, Stock Standard Solutions (approximately 100 μg/ml carbonate ion) is produced as follows:

Accurately weigh approximately 35.4 mg of sodium carbonate and transfer into a 200 mL volumetric flask. Add approximately 100 mL of Standard Diluent to the flask and sonicate for five minutes to dissolve. Allow to cool inside a glove box under nitrogen. Dilute to volume (200 mL) with Standard Diluent.

For the present example, carbonate working standard solutions are prepared as follows:

Working Standard A (Approximately 1.5 μg/ml of Carbonate Ion): Pipette 3.0 ml of Stock Standard Solution into a 200 mL volumetric flask. Dilute to volume with Standard Diluent and mix well.

Working Standard B (Approximately 6 μg/ml of Carbonate Ion): Pipette 6.0 ml of Stock Standard Solution into a 100 mL volumetric flask. Dilute to volume with Standard Diluent and mix well.

Working Standard C (Approximately 12 μg/ml of Carbonate Ion): Pipette 12.0 ml of Stock Standard Solution into a 100 mL volumetric flask. Dilute to volume with Standard Diluent and mix well.

Working Standard D (Approximately 24 μg/ml of Carbonate Ion): Pipette 12.0 ml of Stock Standard Solution into a 50 mL volumetric flask. Dilute to volume with Standard Diluent and mix well.

Working Standard E (Approximately 30 μg/ml of Carbonate Ion): Pipette 15.0 ml of Stock Standard Solution into a 50 mL volumetric flask. Dilute to volume with Standard Diluent and mix well.

Standard C Recovery (Approximately 12 μg/ml of Carbonate Ion): Pipette 12.0 ml of Stock Standard Solution into a 100 mL volumetric flask. Dilute to volume with Standard Diluent and mix well.

A standard diluent blank is prepared by purging Methanol/Water (30%: 70%, v/v) with helium.

Ion Chromatography

The IC is set up as set forth in Example 1, except an injection volume of 25 μL is used. An exemplary chromatographic sequence is shown in Table 3, starting with the injections used to prepare the calibration curve. Because the sample preparation for this example only involves dilution with Sample Diluent, which is the same as the Standard Diluent, the standard diluent blank is used as the blank for both the calibration curve sequence and the sample sequence. As with Example 1, it should be understood that multiple blanks, standards, and/or sample injections can be used, with the average results of each type used in the calculations. However, as with Example 1, if only one blank injection of a given type yields a peak area for carbonate ion, use that peak area rather than an average.

TABLE 3

Exemplary Chromatographic Sequence(s)-Amphetamine API

| Injection Number | Description |
|---|---|
| Standard Calibration Curve: | |
| 1 | Standard Blank |
| 2 | STD A |
| 3 | STD B |
| 4 | STD C |
| 5 | STD D |
| 6 | STD E |
| 7 | STD C Recovery |
| Sample Sequence: | |
| 1 | Standard Blank |
| 2 | Sample |
| 3 | Standard Blank |
| 4 | STD C Recovery |

Calculation of Amphetacarbamate

To determine the amount of amphetacarbamate in the original sample, a power regression line is plotted from the peak area response of carbonate ion versus concentration for the five working standard solution (STD A, B, C, D and E) injections. The y-intercept, slope and correlation coefficient of the regression line are calculated according to the same power equations as in Example 1. The concentration of carbonate (x), is expressed in exponential form as in Equation 3 of Example 1. The % amphetacarbamate in the amphetamine API used to prepare the sample is calculated based on the amount of carbonate ion detected according to the equations below:

$$\text{mg Carbonate} = e^{\frac{\ln(A_{SPL}) - \ln(a)}{b}} \times \frac{V}{1000}$$

$$\text{\% Amphetacarbamate} = \frac{\text{mg Carbonate} \times 2.96967}{W} \times 100$$

where:

$A_{SPL}$=Peak area response of carbonate ion from the sample injection minus peak area response of carbonate ion from the standard blank injection prior to the sample injection (if any);

ln(a)=y-intercept;

b=slope;

V=Sample Volume (100 mL);

W=Sample Weight (mg) (300 mg in this example)

1000=unit conversion from g to mg;

100=unit conversion to percent; and 2.96967=ratio of molecular weight of amphetacarbamate to molecular weight of carbonate ion (178.21/60.01).

System Suitability

System suitability and peak symmetry can be evaluated as discussed for Example 1. The % recovery of a carbonate working standard can be calculated as a check on the working standard, as illustrated by the Standard C Recovery solution in Table 3. In this example, the goal for the target % recovery for the Standard C Recovery solution is not to exceed 5%.

Example 3—Transdermal Amphetamine Composition with Low Levels of Amphetamine Carbamate A transdermal amphetamine composition is prepared under conditions that limit exposure to $CO_2$ as described above, including (i) preparing the wet polymer matrix blend by a staged process that comprises adding the amphetamine API last; (ii) adjusting the oven drying temperature (wherein a higher oven drying temperature generally leads to a shorter drying time that thereby limits exposure to $CO_2$), (iii) adjusting the oven airflow (fan speed) (wherein a higher oven airflow generally leads to a shorter drying time that thereby limits exposure to $CO_2$), (iv) adjusting the web speed (wherein a faster web speed generally limits exposure to $CO_2$), and (v) maintaining the manufacturing room temperature at 60-72° F. Additionally, the oven humidity is maintained at 3-8% relative humidity (RH) and the manufacturing room humidity is maintained at 45-70% RH. A manufacturing overage of about 30% amphetamine is used to prepare the wet polymer matrix blend in order to achieve a target amphetamine content of about 15% in the dry polymer matrix of the final product.

The amphetamine carbamate content of the drug-containing polymer matrix is assessed by ion chromatography as described above, and the amphetacarbamate content is determined to be less than 3.0% of the target amphetamine content, and less than 0.5% wt/wt of the dry polymer matrix.

Example 4—Transdermal Amphetamine Composition with Added Amphetamine Carbamate

To assess the impact of amphetacarbamate/amphetamine carbamate on the physical properties of transdermal amphetamine compositions, transdermal amphetamine systems were prepared without limiting exposure to $CO_2$, on a laboratory scale using varying amounts of added amphetamine carbamate and amphetamine, to achieve a target content of both together of about 15% in the dry polymer matrix. To prepare the added amphetamine carbamate, amphetamine carbamate was prepared by exposing amphetamine to carbon dioxide, which readily leads to the formation of amphetamine carbamate. The other polymer matrix components were two non-acid functional acrylic pressure-sensitive adhesives, GELVA® 3087 (67.50% wt/wt) and DURO-TAK® 87-900A (17.50% wt/wt). (A 15% manufacturing overage of amphetamine was used to achieve the target amounts of amphetamine in the dry polymer matrix.) The "added amphetacarbamate" content was calculated based on the relative molecular weights of amphetamine carbamate and amphetacarbamate, using 314.429 g/mol as the molecular weight for amphetamine carbamate and 179.219 as the molecular weight for amphetacarbamate (based on the difference between the molecular weight of amphetamine carbamate and amphetamine [314.429−135.21=179.219 g/mol], and reported as % of the target amphetamine content of 15% wt/wt of the dry polymer matrix.

| Formulation | Added Amphetamine Carbamate/ Amphetamine Content (% wt/wt of dry polymer matrix) | Added Amphetacarbamate Content (% of target amphetamine content of 15% wt/wt of dry polymer matrix) |
|---|---|---|
| 1 | 0.00 / 15.00 | 0.00 |
| 2 | 0.50 / 14.50 | 1.90 |
| 3 | 1.00 / 14.00 | 3.80 |
| 4 | 1.50 / 13.50 | 5.70 |
| 5 | 2.00 / 13.00 | 7.60 |
| 6 | 2.50 / 12.50 | 9.50 |
| 7 | 3.00 / 12.00 | 11.40 |
| 8 | 6.00 / 9.00 | 22.80 |
| 9 | 9.00 / 6.00 | 34.20 |
| 10 | 12.00 / 3.00 | 45.60 |
| 11 | 15.00 / 0.00 | 57.00 |

Figure 13A:
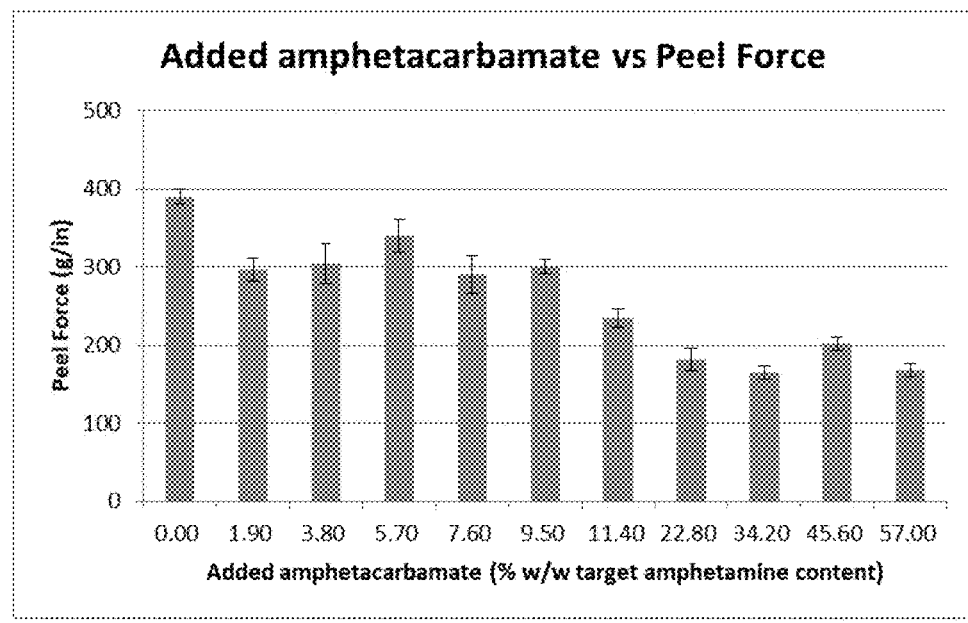
FIG. 13A-13C depict results of testing of amphetamine transdermal systems made with increasing amounts of added amphetamine carbamate, with FIG. 13A reporting results in peel force testing, FIG. 13B reporting results of shear adhesion testing, and FIG. 13C reporting results of probe-tack testing.
Figure 13B:
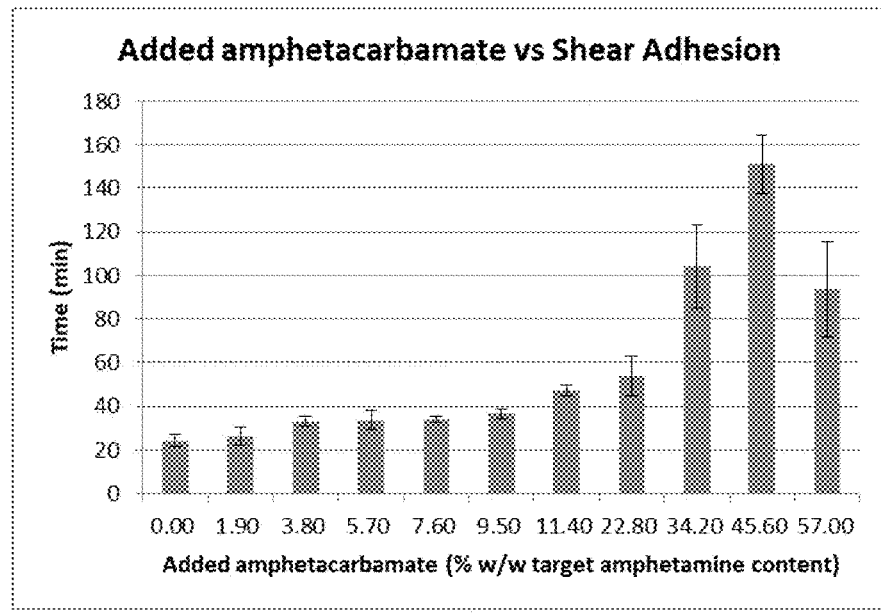
Figure 13C:
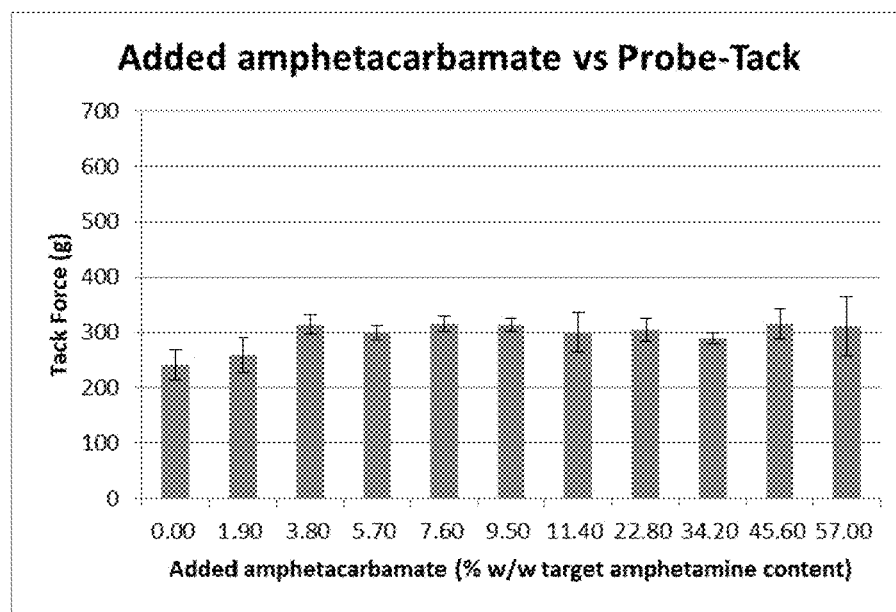

Physical properties including peel force, shear adhesion, and probe-tack were assessed by standard methods. The amphetamine carbamate content was found to have the most impact on shear adhesion, with some impact on peel force also being seen, with properties deteriorating with increasing amphetamine carbamate content as shown in FIGS. 13A-13C, with FIG. 13A reporting results of peel force testing (decreased peel force with increasing amphetamine carbamate/amphetacarbamate), FIG. 13B reporting results of shear adhesion testing (increased shear adhesion with increasing amphetamine carbamate/amphetacarbamate), and FIG. 13C reporting results of probe-tack testing (no significant effect observed).

Example 5—Transdermal Amphetamine Compositions with Varying Levels of Amphetacarbamate The final amphetacarbamate content of transdermal amphetamine compositions prepared as described in Example 4 above was assessed by ion chromatography as described above. The composition with no added amphetamine carbamate was determined to have an amphetacarmbamate content of about 2.5% of the target amount of amphetamine. (Transdermal amphetamine compositions prepared by conventional methods on a commercial scale were found to have an amphetacarmbamate content as high as 12% w/w of the target amount of amphetamine, which was 15% w/w of the dry polymer matrix.) Compositions with an amphetacarbamate content greater than 4% w/w of the target amphetamine content, including compositions having an amphetacarbamate content of 4.5% w/w or 5.0% w/w or greater, than the target amphetamine content, were susceptible to the formation of crystals.

Figure 14A:
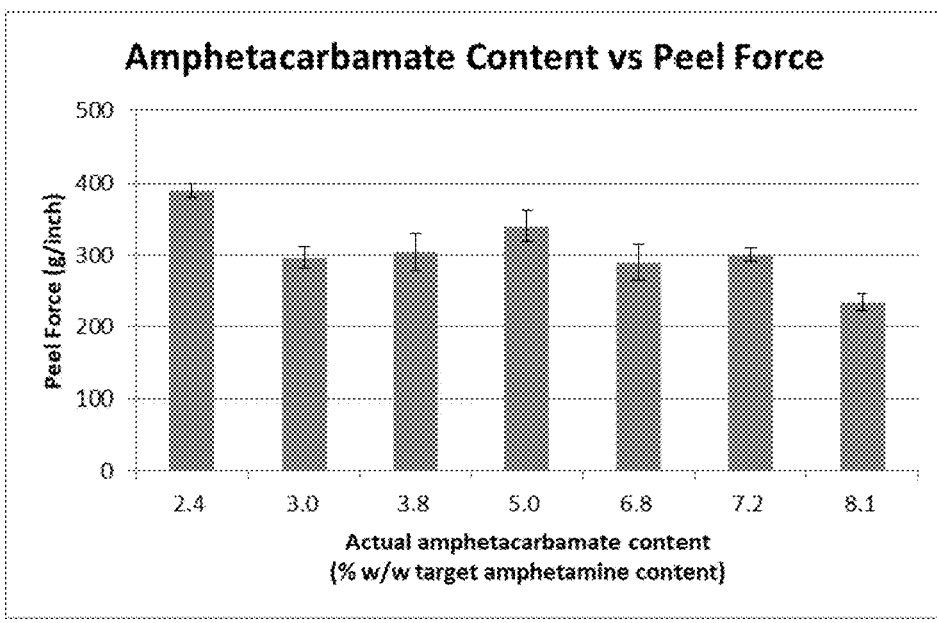
FIG. 14A-14C depict results of testing of amphetamine transdermal systems having increasing amounts of amphetamine carbamate, with FIG. 14A reporting results in peel force testing, FIG. 14B reporting results of shear adhesion testing, and FIG. 14C reporting results of probe-tack testing.
Figure 14B:
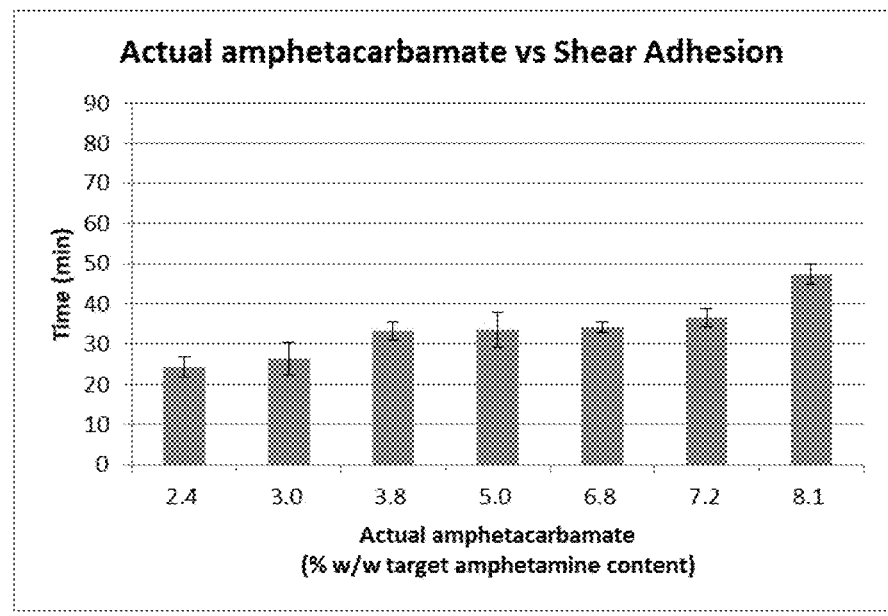
Figure 14C:
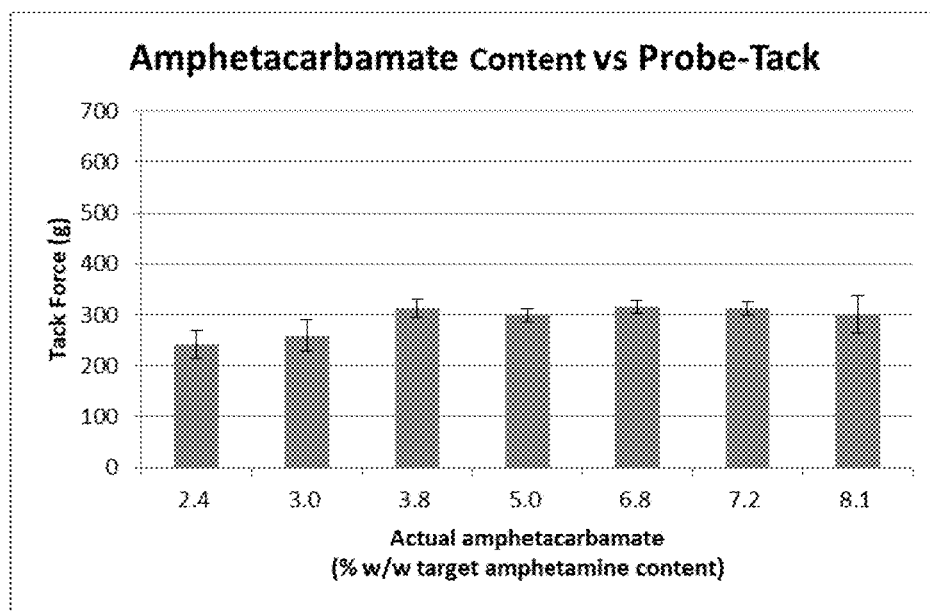

Physical properties including peel force, shear adhesion and probe-tack were assessed by standard methods. The results are shown in FIGS. 14A-14C, with FIG. 14A reporting results in peel force testing (decreased peel force with increasing amphetamine carbamate/amphetacarbamate), FIG. 14B reporting results of shear adhesion testing (increased shear adhesion with increasing amphetamine carbamate/amphetacarbamate), and FIG. 14C reporting results of probe-tack testing (no significant effect observed). The results indicate that a higher amphetamine carbamate content in the drug-containing polymer matrix negatively impacts physical properties including shear adhesion and peel force.

Example 6—Transdermal Amphetamine Compositions Prepared Under Controlled Conditions Transdermal amphetamine compositions were prepared with a target amphetamine content of 15% w/w of the dry polymer matrix, by methods disclosed herein to limit exposure to $CO_2$. In particular, the polymer matrix blend was prepared under a nitrogen blanket, and the drying conditions were adjusted to shorten the drying time by increasing the drying temperature. The amphetacarbamate content of the finished product was assessed by ion chromatography as described above. Results are reported below for each of six lots:

| Lot | Amphetacarbamate Content (% of target amphetamine content of 15% wt/wt of dry polymer matrix) |
|---|---|
| 1 | 1.2 |
| 2 | 1.8 |
| 3 | 1.0 |
| 4 | 1.7 |
| 5 | 1.2 |
| 6 | 1.3 |

The results show that the methods described herein are useful for preparing transdermal amphetamine compositions with a reduced content of amphetacarbamate/amphetamine carbamate than conventional methods, including an amphetacarbamate content of less than 3% w/w of the target amphetamine content of the drug-containing polymer matrix at the time of manufacture.

What is claimed is:

1. A method of making a transdermal amphetamine composition with reduced amphetacarbamate content, comprising:
preparing a transdermal amphetamine composition comprising a drug-containing polymer matrix comprising a therapeutically effective amount of amphetamine in a pressure-sensitive adhesive polymer matrix under conditions that limit exposure to $CO_2$,
wherein the drug-containing polymer matrix has reduced amphetammonium-amphetacarbamate content, determined as one or both of (i) an amphetacarbamate content of from 0.5-5% w/w of the actual amphetamine content of the drug-containing polymer matrix and/or (ii) an amphetacarbamate content of from 0.5-5% w/w of the target amphetamine content of the drug-containing polymer matrix,
wherein the drug-containing polymer matrix is substantially free of visible crystals of amphetamine carbamate.

2. The method of claim 1, wherein the transdermal amphetamine composition is prepared by a process comprising
(i) preparing a drug-containing polymer matrix blend by blending the polymer matrix components and drug in a suitable solvent;
(ii) coating the blend onto a release liner; and
(iii) drying the blend in an oven at a drying temperature to remove the solvent(s), thereby obtaining dry drug-in-polymer matrix on a release liner;
wherein the conditions that limit exposure to $CO_2$ are one or more selected from:
controlling the temperature of the manufacturing room;
preparing the drug-containing polymer matrix under an inert gas;
preparing the drug-containing polymer matrix blend in stages comprising a first stage comprising blending some or all of the polymer matrix components other than amphetamine and a subsequent stage comprising adding and blending in the amphetamine;
adjusting the drying the temperature in the oven
adjusting air flow in the oven; and
adjusting the speed at which the wet polymer matrix material travels along the processing line.

3. The method of claim 1, wherein the drug-containing polymer matrix has an amphetacarbamate content of no more than 1.0% w/w, based on the total dry weight of the drug-containing polymer matrix (% w/w dry).

4. The method of claim 1, wherein the drug-containing polymer matrix has an amphetacarbamate content of no more than 5% w/w of the actual amphetamine content of the drug-containing polymer matrix.

5. The method of claim 1, wherein the drug-containing polymer matrix has an amphetacarbamate content of no more than 3.0% w/w of the target amphetamine content at the time of manufacture.

6. The method of claim 1, wherein, at the time of manufacture, the drug-containing polymer matrix has an amphetacarbamate content of no more than 3.0% w/w of the actual amphetamine content.

7. The method of claim 1, wherein at the time of manufacture the drug-containing polymer matrix has an amphetacarbamate content of from 0.5-5% w/w of the actual amphetamine content.

8. The method of claim 1, wherein, at the time of manufacture the drug-containing polymer matrix has an amphetacarbamate content of from 0.5-5% w/w of the target amphetamine content, and, after storage for six months at ambient conditions in a sealed pouch that is substantially impervious to carbon dioxide, the drug-containing polymer matrix has an amphetacarbamate content of no more than 5.0% of the target amphetamine content.

9. The method of claim 1, wherein the drug-containing polymer matrix has a target amphetamine content or actual amphetamine content at the time of manufacture of from 5% to 20% w/w dry.

10. The method of claim 1, wherein the drug-containing polymer matrix has a target amphetamine content or actual amphetamine content at the time of manufacture of 15% w/w dry.

11. The method of claim 1, wherein the amphetamine is d-amphetamine.

12. The method of claim 1, wherein the drug-containing polymer matrix has a shear adhesion less than that of a comparator drug-containing polymer matrix layer having the same polymer matrix components but a higher amphetacarbamate content, when assessed by the same shear adhesion test.

13. The method of claim 1, wherein the drug-containing polymer matrix has a peel force greater than that of a comparator drug-containing polymer matrix layer having the same polymer matrix components but a higher amphetacarbamate content, when assessed by the same peel adhesion test.

14. The method of claim 1, wherein the pressure-sensitive adhesive polymer component of the drug-containing polymer matrix consists of one or more non-functional acrylic polymers free of vinyl acetate moieties.

15. The method of claim 1, wherein the pressure-sensitive adhesive polymer component of the drug-containing polymer matrix consists of one or more non-functional acrylic polymers free of vinyl acetate moieties, including at least one acrylic polymer polymerized from monomers that include both (i) a soft acrylic monomer having a glass transition temperature ($T_g$) from −70° C. to −10° C. in an amount from 20-70% by weight of the polymer; and (ii) a hard acrylic monomer having a $T_g$ from −5° C. to 120° C. in an amount from 30-80% by weight of the polymer.

16. The method of claim 15, wherein:
(i) the soft acrylic monomer is one or more is selected from 2-ethyl hexyl acrylate, isobutyl acrylate, ethyl acrylate, butyl acrylate, dodecyl methacrylate, 2-ethylhexyl methacrylate, 2-ethoxyethyl acrylate, isopropyl acrylate, and 2-methoxyethyl acrylate, and
(ii) the hard acrylic monomer is one or more selected from methacrylate, N-butyl acrylate, acrylic acid, butyl methacrylate, ethyl methacrylate, methyl methacrylate, hexyl methacrylate, and methyl acrylate.

17. The method of claim 16, wherein the pressure-sensitive adhesive polymer component of the drug-containing polymer matrix consists of one or more non-functional acrylic polymers free of vinyl acetate moieties polymerized from monomers that consist of both monomers selected from said soft acrylic monomers (i) and said hard acrylic monomers (ii).

18. A transdermal amphetamine composition with reduced amphetacarbamate content, prepared by a method according to claim 1.

19. An amphetamine transdermal drug delivery system comprising a transdermal amphetamine composition with reduced amphetacarbamate content prepared by a method according to claim 1 and a backing layer.

20. A method of making a transdermal amphetamine composition with reduced amphetacarbamate content, comprising:
preparing a transdermal amphetamine composition comprising a drug-containing polymer matrix comprising a therapeutically effective amount of amphetamine in a pressure-sensitive adhesive polymer matrix under conditions that limit exposure to $CO_2$, wherein
the drug-containing polymer matrix has an amphetacarbamate content of no more than 1.0% w/w, based on the total dry weight of the drug-containing polymer matrix (% w/w dry), no more than 4% w/w of the actual amphetamine content of the drug-containing polymer matrix, and/or no more than 4% w/w of the target amphetamine content of the drug-containing polymer matrix at the time of manufacture, wherein the drug-containing polymer matrix is substantially free of visible crystals of amphetamine carbamate.

21. A method of transdermally delivering amphetamine, comprising topically applying to a skin surface of a subject in need thereof, an amphetamine transdermal drug delivery system according to claim 19.

22. The method of claim 1, wherein the drug-containing polymer matrix has an amphetacarbamate content of from 0.5-5% w/w of the actual amphetamine content of the drug-containing polymer matrix.

23. The method of claim 1, wherein the drug-containing polymer matrix has an amphetacarbamate content of from 0.5-5% w/w of the target amphetamine content of the drug-containing polymer matrix.

24. The method of claim 1, wherein at the time of manufacture, the drug-containing polymer matrix has an amphetacarbamate content of from 0.5-5% w/w of the target amphetamine content.

25. The method of claim 1, wherein the drug-containing polymer matrix has an amphetacarbamate content of no more than 3.0% w/w of the target amphetamine content.

26. The method of claim 1, wherein the drug-containing polymer matrix has an amphetacarbamate content of no more than 3.0% w/w of the actual amphetamine content.

27. The method of claim 1, wherein the amphetamine is 1-amphetamine.

* * * * *